(12) United States Patent
Takeoka et al.

(10) Patent No.: US 8,241,647 B2
(45) Date of Patent: Aug. 14, 2012

(54) AMPHIPHILIC MOLECULE, MOLECULAR ASSEMBLY COMPRISING THE AMPHIPHILIC MOLECULE, AND USE OF THE MOLECULAR ASSEMBLY

(75) Inventors: Shinji Takeoka, Tokyo (JP); Yosuke Obata, Tokyo (JP); Shoji Tajima, Tokyo (JP); Manabu Ito, Tokyo (JP); Atsushi Mizuno, Tokyo (JP); Natsuko Nishiyama, Tokyo (JP); Yoshito Takeuchi, Tokyo (JP)

(73) Assignees: Waseda University, Tokyo (JP); JCR Pharmaceuticals Co. Ltd., Ashiya-Shi (JP)

(*) Notice: Subject to any disclaimer, the term of this patent is extended or adjusted under 35 U.S.C. 154(b) by 173 days.

(21) Appl. No.: 12/451,555

(22) PCT Filed: May 16, 2008

(86) PCT No.: PCT/JP2008/059499
§ 371 (c)(1),
(2), (4) Date: Feb. 17, 2010

(87) PCT Pub. No.: WO2008/143339
PCT Pub. Date: Nov. 27, 2008

(65) Prior Publication Data
US 2010/0209458 A1    Aug. 19, 2010

(30) Foreign Application Priority Data
May 17, 2007  (JP) ................................. 2007-132179

(51) Int. Cl.
*A61K 9/00*       (2006.01)
*C08G 69/26*      (2006.01)
(52) U.S. Cl. ....................................... 424/400; 528/332
(58) Field of Classification Search .................. None
See application file for complete search history.

(56) References Cited

U.S. PATENT DOCUMENTS

| 5,998,482 | A  | * | 12/1999 | David et al. ................... 514/626 |
| 6,933,352 | B2 | * | 8/2005  | Tsuchida et al. .............. 525/420 |
| 6,949,663 | B2 |   | 9/2005  | Tsuchida et al. |
| 6,965,049 | B2 | * | 11/2005 | Tsuchida et al. .............. 560/170 |
| 7,939,505 | B2 | * | 5/2011  | Quay et al. .................... 514/44 R |
| 2002/0120096 | A1 | * | 8/2002 | Tsuchida et al. .............. 528/332 |
| 2004/0028638 | A1 |   | 2/2004 | Tsuchida et al. |
| 2004/0162261 | A1 | * | 8/2004 | Tsuchida et al. ................ 514/44 |
| 2005/0154514 | A1 |   | 7/2005 | Niessen et al. |

FOREIGN PATENT DOCUMENTS

| EP | 1420010 A1 * | 5/2004 |
| EP | 1938843 A1 * | 7/2008 |
| JP | 2005-154514 A | 6/2005 |
| JP | 2007-210953 A | 8/2007 |
| WO | 01/16211 A1 | 3/2001 |
| WO | 02/38530 A1 | 5/2002 |
| WO | 03/018539 A1 | 3/2003 |
| WO | 03/078383 A1 | 9/2003 |
| WO | WO 03078383 A1 * | 9/2003 |

OTHER PUBLICATIONS

Maeda N, Takeuchi Y, Takada M, Namba Y, Oku N. Synthesis of angiogenesis-targeted peptide and hydrophobized polyethylene glycol conjugate. Bioorg Med Chem Lett. Feb. 23, 2004;14(4):1015-7.*
D. Paphadjopoulos et al., Biochemistry, 24 (1985) 3091-3098.
D.H. Thompson et al., Langmuir, 19 (2003) 6408-6415.
G. Shi et al., Journal of Controlled Release 80 (2002) 309-319.

* cited by examiner

*Primary Examiner* — Robert A Wax
*Assistant Examiner* — Olga V Tcherkasskaya
(74) *Attorney, Agent, or Firm* — McDermott Will & Emery LLP

(57) ABSTRACT

The present invention provides an amphiphilic molecule having a plurality of zwitterionic functional groups in its hydrophilic moiety and a molecular assembly comprising the amphiphilic molecule as a constituent lipid. The molecular assembly of the present invention forms a stable vesicular structure under a physiological pH environment to carry a substance of interest in the vesicular structure, and can release the substance of interest to the outside of the vesicular structure when it is deformed under an acidic pH environment. The molecular assembly of the present invention can be used as a carrier for a drug, a probe, a nucleic acid, a protein or the like.

14 Claims, 8 Drawing Sheets
(1 of 8 Drawing Sheet(s) Filed in Color)

AMPHIPHILIC MOLECULE, MOLECULAR ASSEMBLY COMPRISING THE AMPHIPHILIC MOLECULE, AND USE OF THE MOLECULAR ASSEMBLY

CROSS-REFERENCE TO PRIOR APPLICATION

This is a U.S. National Phase Application under 35 U.S.C. §371 of International Patent Application No. PCT/JP2008/059499 filed May 16, 2008, which claims the benefit of Japanese Patent Application No. 2007-132179 filed May 17, 2007, both of which are incorporated by reference herein. The International Application was published in Japanese on Nov. 27, 2008 as WO2008/143339 A1 under PCT Article 21(2).

FIELD OF THE INVENTION

The present invention relates to an amphiphilic molecule, which is used as a constituent of a molecular assembly capable of controlling release behavior of a substance carried in the molecular assembly in response to changes in pH, a molecular assembly comprising the amphiphilic molecule, and use of the molecular assembly.

BACKGROUND

Heretofore, in methods for controlling release of a substance of interest carried in a molecular assembly such as liposome, pH responsiveness has been widely used. In this regard, "pH responsiveness" refers to characteristics of a molecular assembly in which the molecular packing state, property of releasing a substance carried and the like are changed in response to changes in pH. In particular, pH-responsive liposome using phosphatidylethanolamine-type phospholipid is well known (for example, see: D. Papahadjopoulos et al., Biochemistry, 24 (1985) 3091-3098; and D. H. Thompson et al., Langmuir, 19 (2003) 6408-6415). This utilizes the property of phosphatidylethanolamine-type phospholipid in which structural transition thereof occurs in response to pH to change the molecular packing state of a liposome bilayer membrane. However, such structural transition does not easily occur in the presence of serum. Therefore, it is not practical for use in vivo.

In addition, as pH-responsive liposome, liposome in which anionic lipid and cationic lipid are mixed together is known (see G Shi et al., Journal of Controlled Release 80 (2002) 309-319). However, since it is required to combine anionic lipid and cationic lipid, it is difficult to adjust pH responsiveness depending on purposes. Moreover, cationic lipid itself has low retentivity in blood and high cytotoxicity. Furthermore, only cationic lipid can be fused with an anionic biomembrane at low pH. Therefore, there is a problem with low degree of fusion of liposome.

SUMMARY OF THE INVENTION

Under the above-described circumstances, it is desired that a pH-responsive molecular assembly, which can carry an agent, nucleic acid or the like, and which can control its release behavior in a simple and easy way, is developed. In particular, a pH-responsive molecular assembly, which can be administered into the blood, is desired.

The present inventors diligently performed research in order to solve the above-described problem, and found that a molecular assembly, which comprises an amphiphilic molecule having a plurality of zwitterionic functional groups in its hydrophilic moiety as a constituent, forms a vesicular structure under a physiological pH environment to carry a substance of interest, and that the zeta potential becomes positive under an acidic pH environment, and by the interaction with an anionic membrane (anionic biomembrane), the vesicular structure is deformed to release the substance of interest to the outside of the vesicular structure. Thus the present invention was achieved. By utilizing this property in a living body, a pH-responsive molecular assembly taken into a cell by endocytosis can interact with an endosome membrane under low pH environment in endosome to allow the carried substance of interest to be released into cytoplasm.

More specifically, the present invention provides the following amphiphilic molecule, molecular assembly, agent, reagent, kit and the like.

[1] An amphiphilic molecule represented by the following formula (I) or (II):

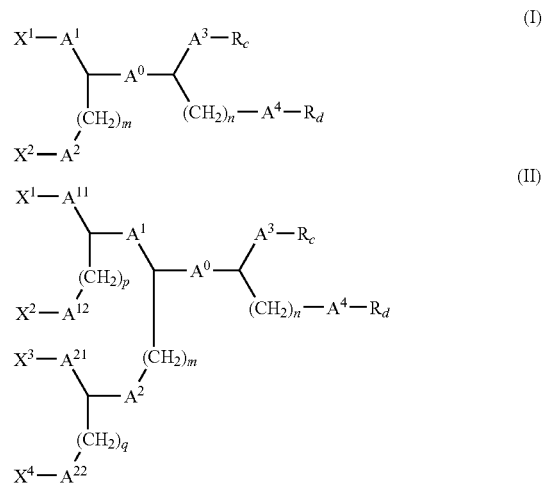

wherein: $X^1$, $X^2$, $X^3$ and $X^4$ each independently represent a zwitterionic functional group; $A^0$, $A^1$, $A^2$, $A^3$, $A^4$, $A^{11}$, $A^{12}$, $A^{21}$ and $A^{22}$ each independently represent —COO—, —OCO—, —CONH— or —NHCO—; Rc and Rd each independently represent a chain hydrocarbon group having 8 to 22 carbon atoms; and m, n, p and q each independently represent an integer from 1 to 4.

[2] An amphiphilic molecule represented by the following formula (Ia):

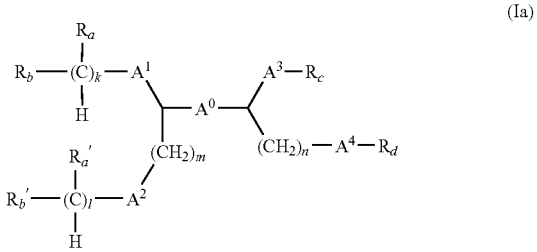

wherein: $R_a$ represents a cationic functional group when the formula has one $R_a$, and when the formula has a plurality of $R_a$s, one of $R_a$s represents a cationic functional group and the other $R_a$s represent a hydrogen atom; $R_a'$ represents a cationic functional group when the formula has one $R_a'$, and when the formula has a plurality of $R_a'$s, one of $R_a'$s represents a cationic functional group and the other $R_a'$s represent a hydrogen atom; $R_b$ and $R_b'$ each independently represent an anionic functional group; $R_c$ and $R_d$ each independently represent a chain hydrocarbon group having 8 to 22 carbon atoms; $A^0$, $A^1$, $A^2$, $A^3$ and $A^4$ each independently represent —COO—, —OCO—, —CONH— or —NHCO—; and k, l, m and n each independently represent an integer from 1 to 4. $A^0$, $A^1$ and $A^2$ each independently are preferably —CONH— or —NHCO—, and more preferably —CONH—. $A^3$ and $A^4$ each independently are preferably —COO— or —OCO—, and more preferably —COO—.

[3] The amphiphilic molecule according to item [2], wherein in an aqueous solution, the cationic functional group and the anionic functional group are independently ionized under a physiological pH environment to become a cation or an anion, and wherein ionization tendency of the anionic functional group is diminished under an acidic pH environment, and wherein ionization tendency of the cationic functional group is diminished under a basic pH environment.

[4] The amphiphilic molecule according to item [2] or [3], wherein the cationic functional group is selected from the group consisting of a primary amino group, a secondary amino group, a tertiary amino group and a quaternary ammonium salt.

[5] The amphiphilic molecule according to any one of items [2] to [4], wherein the anionic functional group is a carboxyl group.

[6] The amphiphilic molecule according to any one of items [2] to [5], wherein: k is 3; l is 3; m is 4; and n is 2.

[7] The amphiphilic molecule according to any one of items [2] to [5], wherein: k is 2; l is 2; m is 4; and n is 2.

[8] The amphiphilic molecule according to any one of items [2] to [5], wherein: k is 3; l is 2; m is 4; and n is 2.

[9] The amphiphilic molecule according to any one of items [2] to [5], wherein: k is 2; l is 3; m is 4; and n is 2.

[10] The amphiphilic molecule according to any one of items [2] to [5], wherein: k is 3; l is 3; m is 4; and n is 1.

[11] The amphiphilic molecule according to any one of items [2] to [5], wherein: k is 2; l is 2; m is 4; and n is 1.

[12] The amphiphilic molecule according to any one of items [2] to [5], wherein: k is 3; l is 2; m is 4; and n is 1.

[13] The amphiphilic molecule according to any one of items [2] to [5], wherein: k is 2; l is 3; m is 4; and n is 1.

[14] The amphiphilic molecule according to any one of items [1] to [13], wherein the chain hydrocarbon group is selected from the group consisting of a myristyl group, a palmityl group, a stearyl group and an oleyl group.

[15] An amphiphilic molecule represented by any one of the following formulae (Ia-1) to (Ia-8):

(Ia-1)
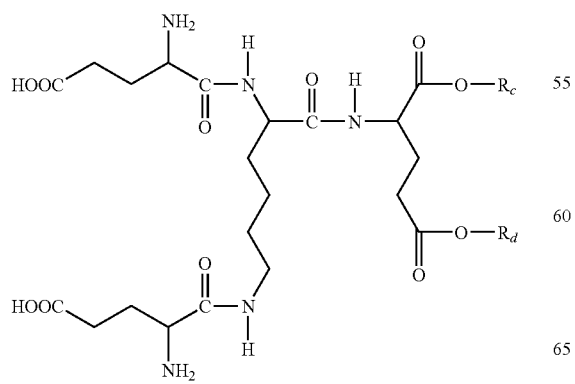

(Ia-2)
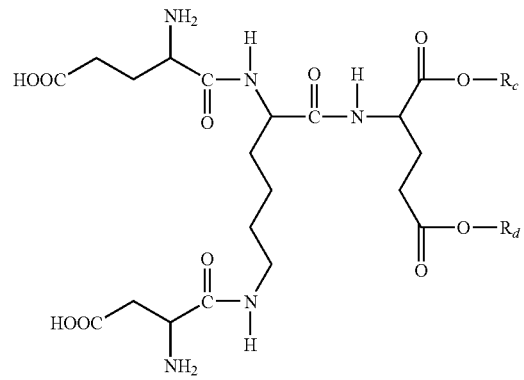

(Ia-3)
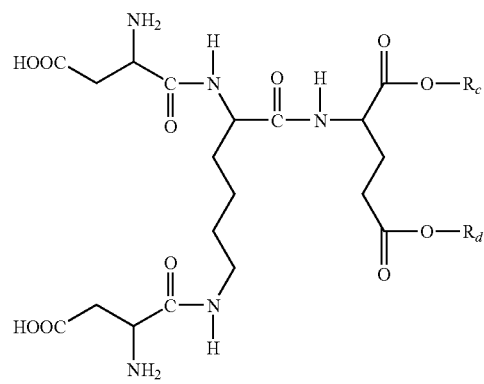

(Ia-4)
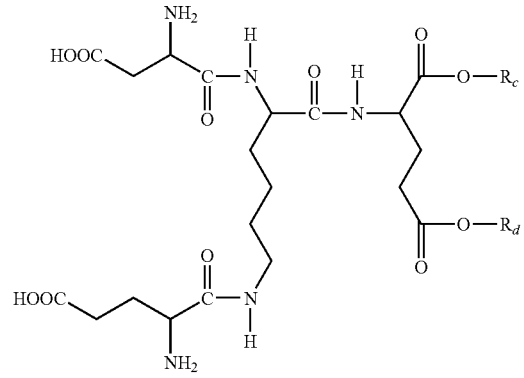

(Ia-5)
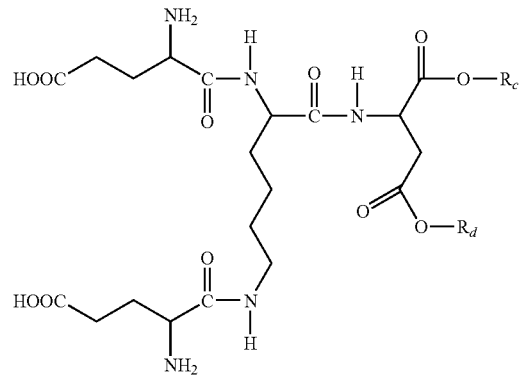

-continued

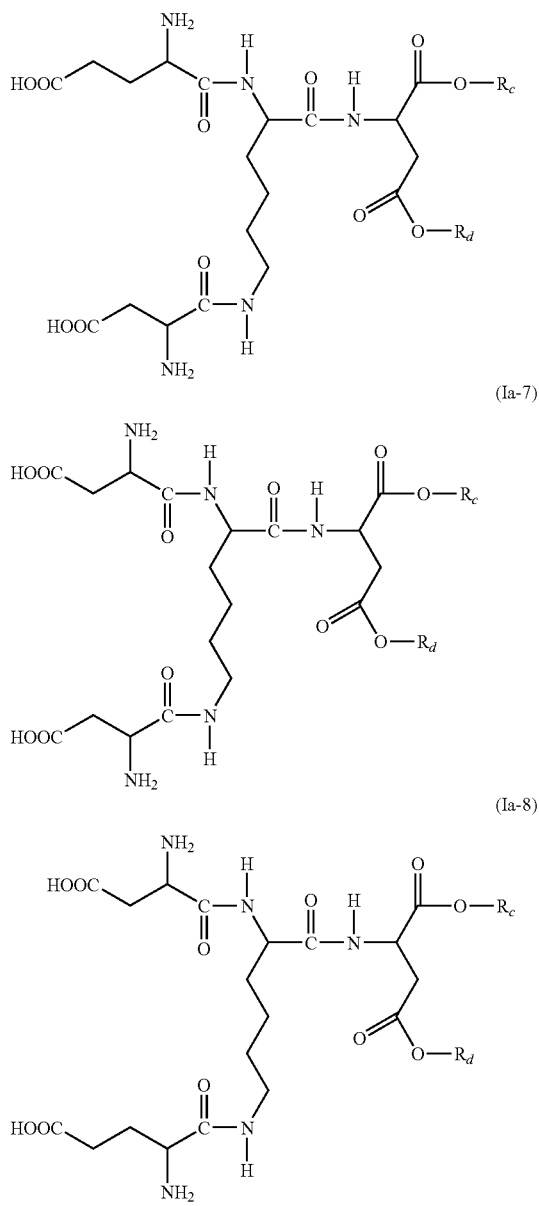

wherein $R_c$ and $R_d$ each independently represent a chain hydrocarbon group having 8 to 22 carbon atoms.

[16] The amphiphilic molecule according to item [15], wherein in an aqueous solution, —NH$_2$ becomes —NH$_3^+$ and —COOH becomes —COO$^-$ under a physiological pH environment to exhibit zwitterionic properties, and wherein ionization tendency of —COOH is diminished under an acidic pH environment, and wherein ionization tendency of —NH$_2$ is diminished under a basic pH environment.

[17] An amphiphilic molecule constituting a molecular assembly, which forms a vesicular structure in which the zeta potential becomes neutral or negative under a physiological pH environment to carry a substance of interest, wherein the zeta potential becomes positive under an acidic pH environment, and by the interaction with an anionic biomembrane, the vesicular structure is deformed to release the substance of interest to the outside of the vesicular structure.

[18] The amphiphilic molecule according to item [17], which is the amphiphilic molecule according to any one of items [1] to [16].

[19] A molecular assembly comprising the amphiphilic molecule according to any one of items [1] to [18]. The molecular assembly preferably carries at least one substance selected from the group consisting of a drug, a probe, a nucleic acid, a protein, a peptide, a metal ion and a metal complex.

[20] The molecular assembly according to item [19], which forms a vesicular structure in which the zeta potential becomes neutral or negative under a physiological pH environment to carry a substance of interest, wherein the zeta potential becomes positive under an acidic pH environment and by the interaction with an anionic biomembrane, the vesicular structure is deformed to release the substance of interest to the outside of the vesicular structure.

[21] The molecular assembly according to item [19] or [20], which releases the substance of interest to the outside of an endosome when taken into a cell by endocytosis.

[22] The molecular assembly according to item [20] or [21], wherein the substance of interest is at least one substance selected from the group consisting of a drug, a probe, a nucleic acid, a protein, a peptide, a metal ion and a metal complex.

[23] An agent comprising the molecular assembly according to item [22].

[24] The agent according to item [23], which is an agent for intravenous administration.

[25] The agent according to item [23], which is an agent for topical administration.

[26] A reagent comprising the molecular assembly according to any one of items [19] to [21], which carries a probe or nucleic acid.

[27] The reagent according to item [26], which controls gene expression in a cell.

[28] A kit comprising the reagent according to item [26] or [27].

[29] A protein preparation for enzyme replacement therapy comprising the molecular assembly according to any one of items [19] to [21], which carries a protein.

According to the present invention, a molecular assembly and an amphiphilic molecule, which have pH responsiveness, can be provided.

According to a preferred embodiment of the present invention, the molecular assembly of the present invention has the release control function in which a substance of interest carried in the molecular assembly is released when the pH value thereof becomes lower than the physiological value. Therefore, the molecular assembly retained in blood or a medium can efficiently release a drug, protein, nucleic acid or the like from an endosome to cytoplasm only when taken into a cell by endocytosis.

According to a preferred embodiment of the present invention, the molecular assembly of the present invention can deliver a substance of interest to the outside of a vesicle and endosome without using a cationic lipid such as N-[1-(2,3-Dioleoyloxy)propyl]-N,N,N-trimethylammonium methylsulfate (DOTAP) and 1,2-Dimyristyloxypropyl-3-dimethylhydroxyethyl ammonium bromide (DMRIE), which tends to be easily adsorbed to a blood vessel wall or the like at the time of retention in blood. Therefore, according to a preferred embodiment of the present invention, the molecular assembly of the present invention shows high degree of fusion with an anionic biomembrane, excellent biocompatibility and retention in blood, and accordingly is excellent in practical utility as an in vivo preparation.

According to a preferred embodiment of the present invention, the amphiphilic molecule of the present invention can be synthesized from amino acid and long-chain alcohol, and therefore, it is considered that the amphiphilic molecule has high blood compatibility and low cytotoxicity. Moreover, there is also an advantage that a pH-responsive molecular assembly can be prepared at low cost using a simple and easy method.

By utilizing the present invention, a course for creation of a highly-functional drug carrier or nucleic acid carrier can be set.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
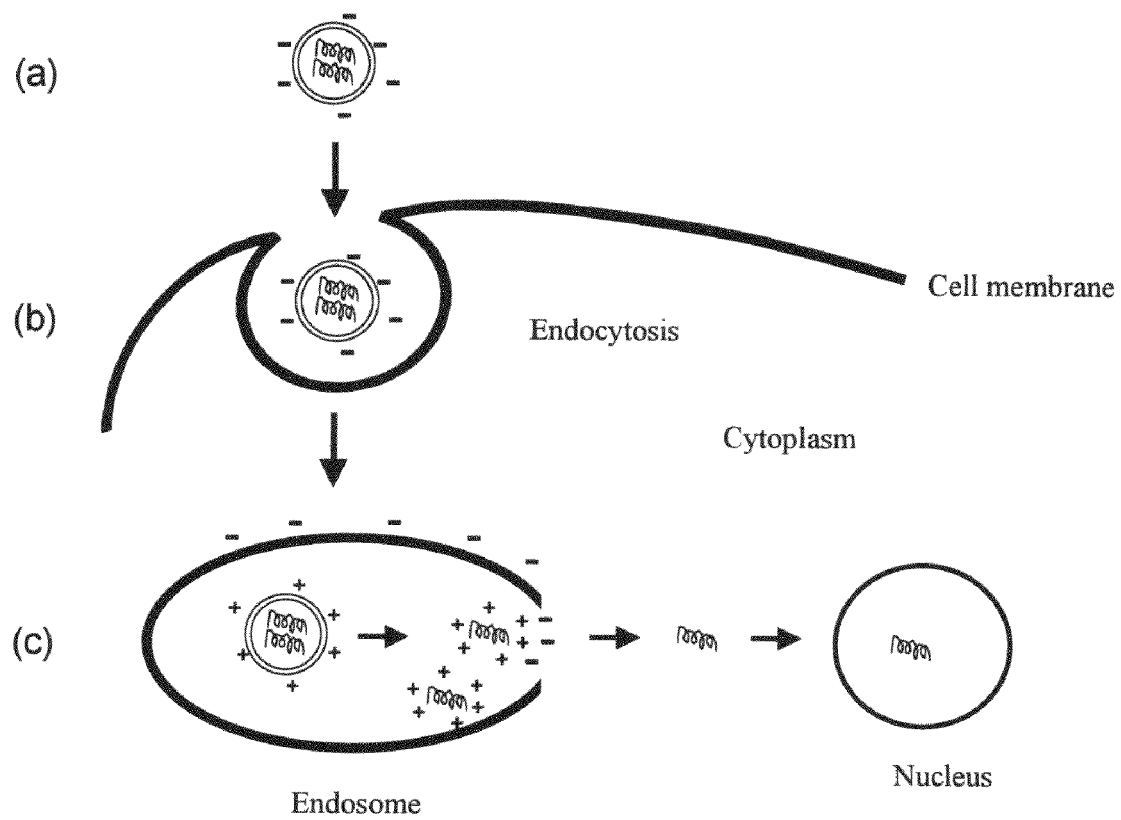
FIG. 1 is a schematic view showing behavior of the molecular assembly of the present invention, wherein after administered into a living body, the molecular assembly of the present invention is retained in the blood to be taken into a target cell and then releases a substance of interest held by the molecular assembly.

Hereinafter, the present invention will be described in detail.

The present invention includes an amphiphilic molecule, a molecular assembly, an agent, a reagent, a kit thereof, etc. Hereinafter, each of these products will be described in detail.

[1] Amphiphilic Molecule

Firstly, the amphiphilic molecule of the present invention will be described.

The amphiphilic molecule of the present invention has a structure represented by the following formula (I) or (II):

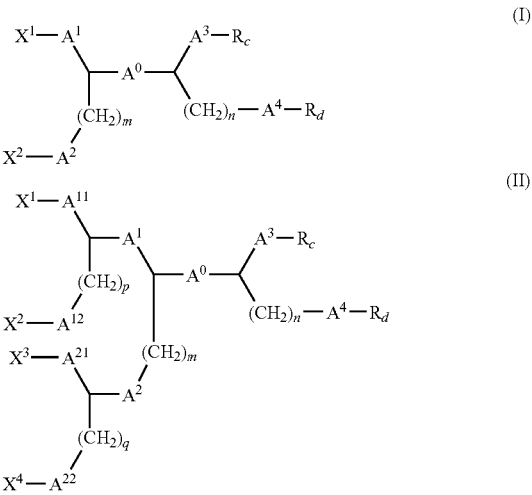

wherein: $X^1$, $X^2$, $X^3$ and $X^4$ each independently represent a zwitterionic functional group; $A^0$, $A^1$, $A^2$, $A^3$, $A^4$, $A^{11}$, $A^{12}$, $A^{21}$ and $A^{22}$ represent —COO—, —OCO—, —CONH— or —NHCO—; $R_c$ and $R_d$ each independently represent a chain hydrocarbon group having 8 to 22 carbon atoms; and m, n, p and q each independently represent an integer from 1 to 4.

As shown by the formula (I) or (II), the amphiphilic molecule of the present invention has a plurality of zwitterionic functional groups in its hydrophilic moiety. In this regard, "zwitterionic functional group" refers to a functional group which has a "cationic functional group" exhibiting cationic properties under a physiological pH environment and an acidic pH environment and an "anionic functional group" showing anionic properties under a physiological pH environment in combination.

As described above, the amphiphilic molecule of the present invention has a plurality of zwitterionic functional groups, and has high cationic or anionic charge density caused by change of pH. Therefore, pH responsiveness of the amphiphilic molecule of the present invention is higher than that of the case of having only one zwitterionic functional group.

Based on the technical idea of the present invention, the number of zwitterionic substituents can be further increased. For example, by further introducing a substituent having zwitterionic substituents $X^5$ and $X^6$ as represented by the following formula:

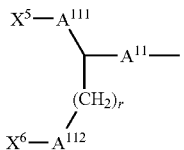

wherein: $X^5$ and $X^6$ each independently represent a zwitterionic functional group; $A^{11}$, $A^{112}$ and $A^{112}$ each independently represent —COO—, —OCO—, —CONH— or —NHCO—; and r is an integer from 1 to 4, to a linkage group $A^{11}$ in the formula (I), zwitterionic functional groups can be dendritically formed in the hydrophilic moiety of the amphiphilic molecule.

According to a preferred embodiment of the present invention, the amphiphilic molecule of the present invention has zwitterionic functional groups in its hydrophilic moiety as described above, and therefore can be neutral under a physiological pH environment, can be cationic under an acidic pH environment, and can be anionic under a basic pH environment.

As used herein, "under a physiological pH environment" means that pH of an aqueous solution is within the range of neutral pH, preferably 6.0 or higher and lower than 8.0, more preferably 7.0 to 7.6, and even more preferably 7.2 to 7.5.

As used herein, "under an acidic pH environment" means that pH of an aqueous solution is lower than neutral pH, preferably lower than 7.2, more preferably lower than 7.0, even more preferably lower than 6.5, particularly preferably lower than 6.0, and most particularly preferably 5.5 or lower.

As used herein, "under a basic pH environment" means that pH of an aqueous solution is higher than neutral pH, and preferably higher than 8.0 and 12 or lower.

In the present invention, the "cationic functional group" is not particularly limited as long as it exhibits cationic properties under a physiological pH environment and an acidic pH environment in an aqueous solution. Examples of such cationic functional groups include amino group, ammonium salt, guanidino group, imidazole group and derivatives thereof. In this regard, "derivative" refers to a compound in which one or more hydrogen atoms of an amino group, ammonium salt, guanidino group or imidazole group are substituted with a substituent such as lower alkyl group (e.g., methyl, ethyl, propyl, isopropyl, n-butyl, iso-butyl, tert-butyl, pentyl, and hexyl), aminoalkyl group (e.g., aminomethyl, aminoethyl, aminopropyl and aminobutyl), alkyl group of oligosaccharide corresponding thereto, hydroxyl group, hydroxylalkyl group (e.g., hydroxymethyl, hydroxyethyl and hydroxypropyl), and oligooxyalkyl group (e.g., oligooxymethyl, oligooxyethyl and oligooxypropyl). Among them, preferred examples of cationic functional groups include a primary amino group (—NH$_2$), a secondary amino group (—NHR), a tertiary amino group (—NR$_2$) and a quaternary ammonium salt (—NR$_3^+$X$^-$). In this regard, Rs each independently represent a lower alkyl group (e.g., methyl, ethyl, propyl, isopropyl, n-butyl, iso-butyl, tert-butyl, pentyl, and hexyl), and X represents a halogen atom or alkyl sulfuric acid having 1 to 2 carbon atoms or p-toluenesulfonic acid. Among them, a primary amino group is particularly preferred.

In the present invention, "anionic functional group" is not particularly limited as long as it exhibits anionic properties under a physiological pH environment and a basic pH environment in an aqueous solution. For example, as such an anionic functional group, a carboxyl group is preferred.

In the present invention, the structure of the zwitterionic functional group is not particularly limited, but is preferably a structure in which the anionic functional group is positioned nearer to the surface side when forming the molecular assembly. More specifically, it is preferred that the cationic functional group and the anionic functional group are bound via a methylene spacer. It is more preferred that a methylene group is bound via 1 or 2 methylene spacers. It is particularly preferred that a structure in which the cationic functional group side binds to the side constituting the hydrophobic moiety.

In one embodiment of the present invention, the amphiphilic molecule of the present invention is preferably represented by the following formula (Ia):

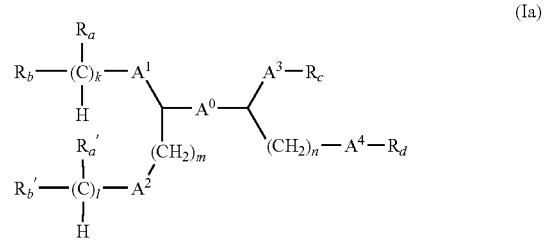

(Ia)

wherein: $R_a$ represents a cationic functional group when the formula has one $R_a$, and when the formula has a plurality of $R_a$s, one of $R_a$s represents a cationic functional group and the other $R_a$s represent a hydrogen atom; $R_a'$ represents a cationic functional group when the formula has one $R_a'$, and when the formula has a plurality of $R_a'$s, one of $R_a'$s represents a cationic functional group and the other $R_a'$s represent a hydrogen atom; $R_b$ and $R_b'$ each independently represent an anionic functional group; and $R_d$ each independently represent a chain hydrocarbon group having 8 to 22 carbon atoms; $A^0$, $A^1$, $A^2$, $A^3$ and $A^4$ each independently represent —COO—, —OCO—, —CONH— or —NHCO—; and k, l, m and n each independently represent an integer from 1 to 4.

According to a preferred embodiment of the present invention, regarding the amphiphilic molecule of the present invention, in an aqueous solution, the cationic functional group and the anionic functional group are independently ionized under a physiological pH environment to become a cation and an anion, respectively. Ionization tendency of the anionic functional group is diminished under an acidic pH environment, and ionization tendency of the cationic functional group is diminished under a basic pH environment. In this regard, "ionization tendency . . . is diminished" means that an ionization ratio becomes lower than that shown under a physiological pH environment.

In the present invention, $A^0$, $A^1$, $A^2$, $A^3$, $A^4$, $A^{11}$, $A^{12}$, $A^{21}$ and $A^{22}$ each independently represent —COO—, —OCO—, —CONH— or —NHCO—. It is preferred that $A^0$, $A^1$, $A^2$, $A^{11}$, $A^{12}$, $A^{21}$ and $A^{22}$ each independently represent —CONH— or —NHCO—, and —CONH— is particularly preferred. When $A^0$, $A^1$, $A^2$, $A^{11}$, $A^{12}$, $A^{21}$ and $A^{22}$ is —CONH—, naturally-occurring amino acids or derivatives thereof can be used as raw materials, and therefore, there is an advantage that low toxicity and low cost can be realized. When describing "-linkage group-" herein, it means that the linkage position at the left side is the hydrophilic moiety and the linkage position at the right side is the hydrophobic moiety. It is preferred that $A^3$ and $A^4$ each independently represent —COO— or —OCO—, and —COO— is particularly preferred. When $A^3$ or $A^4$ is —COO—, naturally-occurring amino acids or derivatives thereof can be used as raw materials, and therefore, there is an advantage that low toxicity and low cost can be realized.

In the present invention, $R_c$ and $R_d$ each independently represent a chain hydrocarbon group having 8 to 22 carbon atoms. The chain hydrocarbon group is not particularly limited as long as it is a hydrophobic group which can be introduced by covalent bond. The chain hydrocarbon group may be linear or branched, and is preferably linear. Further, the chain hydrocarbon group may have one or more substituents selected from the group consisting of an alkyl chain, an alkenyl chain, an alkynyl chain, an isoprenoid chain, a vinyl group, a carboxyl group, a hydroxyl group, an amino group and a mercapto group. The carbon number of the chain hydrocarbon group is preferably 12 to 20, and more preferably 14 to 18. Further, the chain hydrocarbon group may have an unsaturated bond such as a double bond and a triple bond. In this case, the number of unsaturated bonds is preferably 1 to 4. The hydrocarbon chain may be a branched chain. Examples of branched chains include one having an isoprenoid structure at its long chain. In the present invention, the chain hydrocarbon group is preferably selected from the group consisting of a myristyl group, a palmityl group, a stearyl group and an oleyl group, and is particularly preferably a palmityl group. The zeta potential behavior and the degree of fusion with an anionic biomembrane at the time of forming a molecular assembly can be adjusted by the combination of the hydrophilic moiety and the hydrophobic moiety constituted by the chain hydrocarbon group. The chain hydrocarbon group may be suitably selected depending on the combination with the hydrophilic moiety of the amphiphilic molecule, the composition of the molecular assembly, purposes, applications, etc. in consideration of the hydrophobic-hydrophilic balance.

In the present invention, k, l, m, n, p and q each independently represent an integer from 1 to 4. k is preferably 3, and l is preferably 3. When k and l are 3, glutamic acid or a derivative thereof can be used as a raw material, and therefore, there is an advantage that low toxicity and low cost can be realized. When k or l is 2, aspartic acid or a derivative thereof can be used as a raw material, and therefore, low toxicity and low cost can be realized. However, when both k and l are 2, there is a case where it is difficult to form a vesicular structure at the time of forming a molecular assembly. Therefore, it is preferred that one of k and l is 3. The cationic functional group and the anionic functional group may be bound via a methylene spacer. The cationic functional group and the anionic functional group may be bound to the same carbon atom. However, as already described, it is preferred that the cationic functional group and the anionic functional group are bound via a methylene spacer. Further, it is particularly preferred that a methylene group is bound to each other via 1 or 2 methylene spacers.

m, p and q each independently represent an integer from 1 to 4, and are preferably 4. When m, p and q are 4, lysine can be used as a raw material, and therefore, low toxicity and low cost can be realized.

n is an integer from 1 to 4, and is preferably 2 to 4. When n is 2 to 4, it is expected that the chain hydrocarbon group of the amphiphilic molecule of the present invention can be oriented approximately perpendicularly to the membrane plane of a bilayer membrane. In addition, when n is 2 to 4, the hydrophobic-hydrophilic interface of a bilayer membrane formed by assembling of amphiphilic molecules in an aqueous solution is stable, and it is easier to form a vesicular structure. Moreover, when n is 2, glutamic acid and a derivative thereof can be used as a raw material, and therefore, there is an advantage that low toxicity and low cost can be realized. When n is 1, aspartic acid or a derivative thereof can be used as a raw material, and therefore, low toxicity and low cost can be realized. However, it may be more difficult to form a vesicular structure of the molecular assembly compared to the case where n is 2.

Preferred examples of combinations of k, l, m and n in the formula (Ia) (k, l, m, n) include (3, 3, 4, 2), (2, 2, 4, 2), (3, 2, 4, 2), (2, 3, 4, 2), (3, 3, 4, 1), (2, 2, 4, 1), (3, 2, 4, 1) and (2, 3, 4, 1).

Preferred embodiments of the amphiphilic molecule of the present invention are shown below:

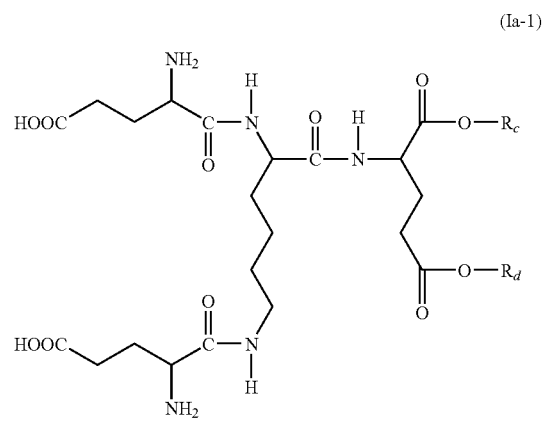

(Ia-1)

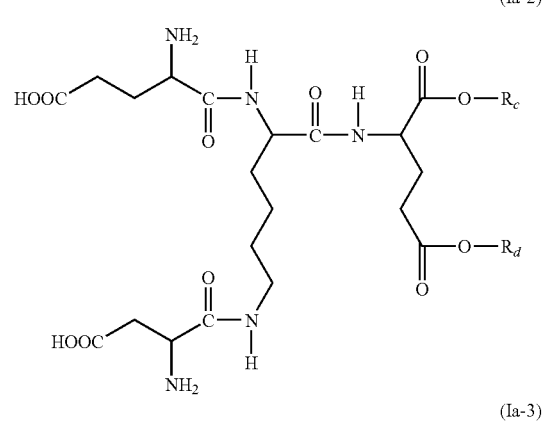

(Ia-2)

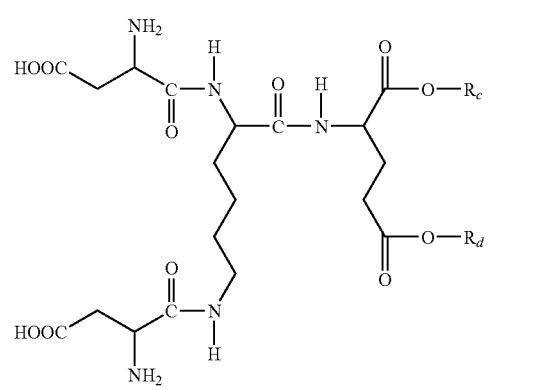

(Ia-3)

-continued

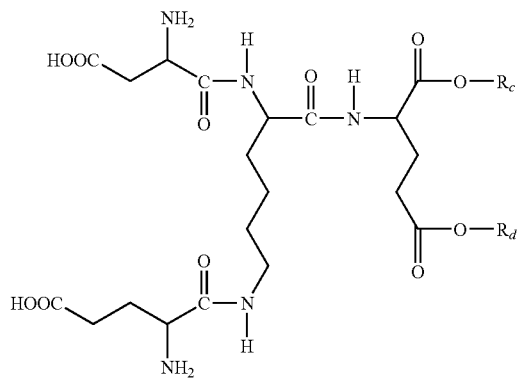
(Ia-4)

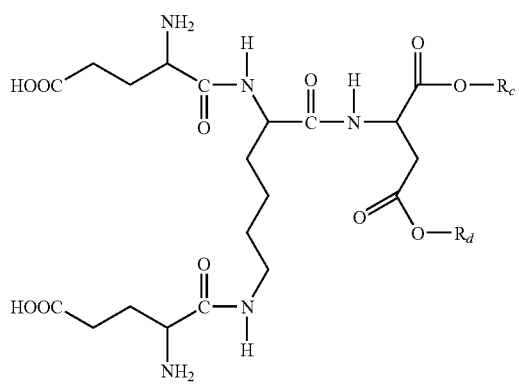
(Ia-5)

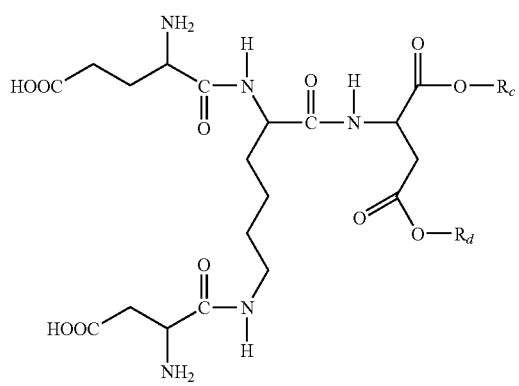
(Ia-6)

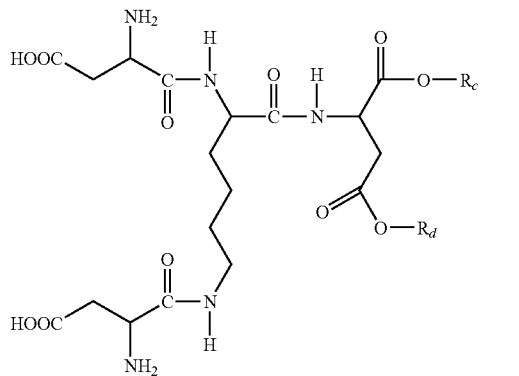
(Ia-7)

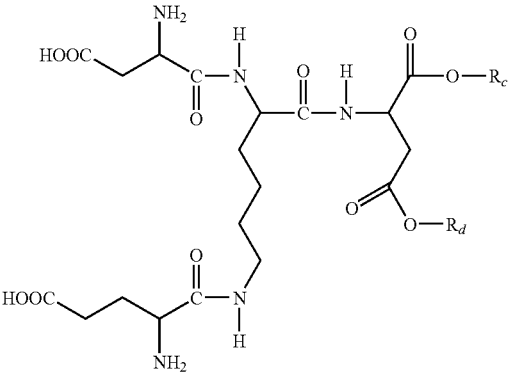
(Ia-8)

[In the formulae, $R_c$ and $R_d$ are as defined above.]

Among them, compounds represented by the above-described formulae (Ia-1), (Ia-2) and (Ia-4) are preferred in the present invention, and compounds represented by the formula (Ia-1) are particularly preferred. Preferred examples of $R_c$ and $R_d$ in the formulae are as described above.

According to a preferred embodiment of the present invention, in the amphiphilic molecule of the present invention represented by any of the formulae (Ia-1) to (Ia-8), —NH$_2$ becomes —NH$_3^+$ and —COOH becomes —COO— under a physiological pH environment in an aqueous solution to exhibit zwitterionic properties. However, ionization tendency of —COOH is diminished under an acidic pH environment, and ionization tendency of —NH$_2$ is diminished under a basic pH environment.

The amphiphilic molecule of the present invention can be produced using a very simple and easy method by combining publicly-known reactions. For example, for the amphiphilic molecule of the present invention, trifunctional compounds are sequentially reacted to prepare a core structure represented by, for example, the following formula (I) or (II):

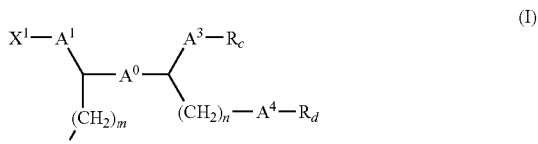
(I)

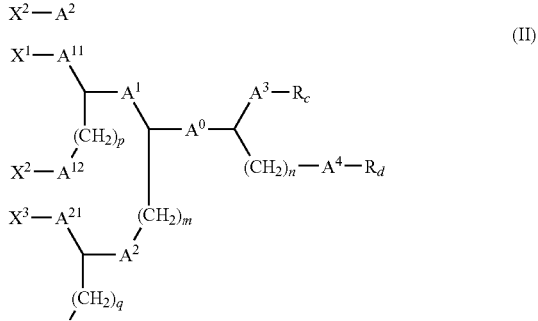
(II)

wherein: $X^1$, $X^2$, $X^3$ and $X^4$ each independently represent a zwitterionic functional group; $A^1$, $A^2$, $A^{11}$, $A^{12}$, $A^{21}$ and $A^{22}$ each independently represent —COO—, —OCO—, —CONH— or —NHCO—; and m, n, p and q each independently represent an integer from 1 to 4. Regarding the chain hydrocarbon group, a source thereof may be introduced in advance by reacting it with one of the trifunctional compounds to be sequentially reacted with other trifunctional compounds. Alternatively, the chain hydrocarbon group may be introduced into a complex consisting of 2 or more trifunctional compounds.

The trifunctional compound to be used in the present invention is not particularly limited as long as it has at least 3 reactive functional groups (e.g., amino group, carboxyl group, and hydroxyl group). Examples thereof include various amino acids (e.g., aspartic acid, glutamic acid, lysine, arginine and histidine) or derivatives thereof, glycerol, oligosaccharides, oligopeptides, polyesters, vinyl-based oligomer, and multibranched structures constituted by them (e.g., dendron structure).

In this regard, the "derivatives of amino acids" include compounds in which a hydrogen atom included in an amino acid is substituted with a substituent such as a lower alkyl group (e.g., methyl, ethyl, propyl, isopropyl, n-butyl, and iso-butyl), an aminoalkyl group (e.g., aminomethyl, aminoethyl, aminopropyl, and aminobutyl) or a corresponding oligoaminoalkyl group, a hydroxyl group, a hydroxyalkyl group (e.g., hydroxymethyl, hydroxyethyl, and hydroxypropyl), and an oligooxyalkyl group (e.g., oligooxymethyl group, oligooxyethyl group, and oligooxypropyl).

For example, an oligopeptide chain constituted by repeat of lysine has any number of amino groups at its side chain, and into them, any number of zwitterionic functional groups can be introduced by amide bond. The hydrophobic moiety can be bound to a carboxyl group at the N-terminus of an oligopeptide chain. In the case of monodendron formed of lysines, the number of functional groups at the terminus can be controlled by the generation number. That is, the number of functional groups is 2 in the case of the first generation, 4 in the case of the second generation, and 8 in the case of the third generation.

The source of the chain hydrocarbon group to be used in the present invention is not particularly limited as long as it is a chain hydrocarbon group having a reactive functional group (e.g., amino group, hydroxyl group, and carboxyl group) which can be covalently-bound to a trifunctional compound or a core structure formed of the trifunctional compounds.

Examples of the source of the chain hydrocarbon group having a carboxyl group to be used in the present invention include: a fatty acid such as acetic acid, propionic acid, butyric acid, valeric acid, isovaleric acid, capronic acid, enanthic acid, caprylic acid, undecanoic acid, lauric acid, tridecanoic acid, myristic acid, pentadecanoic acid, palmitic acid, heptadecanoic acid, stearic acid, nonadecanoic acid, arachic acid, behenic acid, palmitoleic acid, oleic acid, linoleic acid, linolenic acid, arachidonic acid and the like; branched chain forms thereof; and acid anhydrides and acid chlorides thereof.

Examples of the source of the chain hydrocarbon group having an amino group include: a straight chain primary amine such as dodecylamine, tridecylamine, tetradecylamine, pentadecylamine, hexadecylamine, heptadecylamine, octadecylamine, docosylamine, oleylamine and the like; branched chain forms thereof; and an amine such as branched isoprenoid or the like. Examples of the source of an aliphatic hydrocarbon group having an amino group include: a secondary amine such as N-methyl-dodecylamine, N-methyl-tetradecylamine, N-methyl-hexadecylamine, N-ethyl-dodecylamine, N-ethyl-tetradecylamine, N-ethyl-hexadecylamine, N-propyl-dodecylamine, N-propyl-tetradecylamine, N-propyl-hexadecylamine, dioleylamine and the like; and branched chain forms thereof.

Examples of the source of the chain hydrocarbon group having a hydroxyl group include a straight chain primary saturated alcohol such as lauryl alcohol, cetyl alcohol, stearyl alcohol, behenyl alcohol and the like. Examples of other compounds usable as the chain hydrocarbon group having a hydroxyl group include: straight chain primary saturated alcohol such as 1,1-dodecenol, 1-oley alcohol, linolenyl alcohol or the like; branched primary saturated alcohol; branched primary unsaturated alcohol; secondary saturated alcohol; and secondary unsaturated alcohol. Dialkylglycerol obtained by linking such an alcohol to the 1,3-position or 1,2-position of glycerin, and dialkylglycerol formed of a primary saturated alcohol and a primary unsaturated alcohol are also usable.

As the source of the chain hydrocarbon group to be used in the present invention, a sterol is also usable. Examples of the sterol include cholesterol, cholestanol, sitosterol, ergosterol and the like.

A typical synthetic route for the amphiphilic molecule of the present invention is as follows:

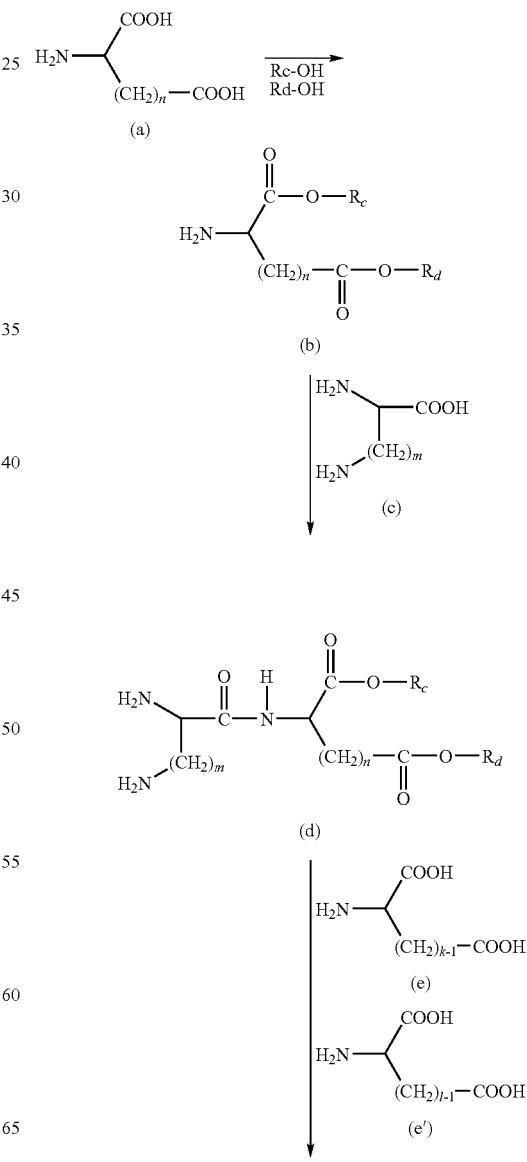

-continued

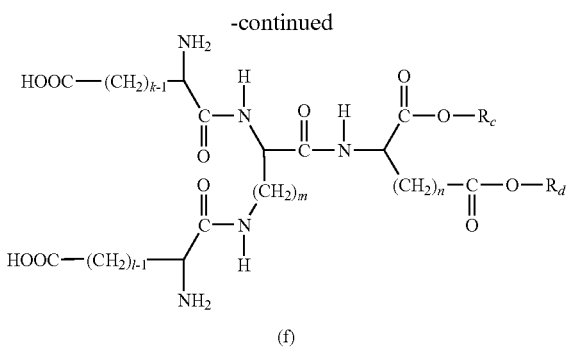

(f)

Firstly, a source of the chain hydrocarbon group (e.g., $R_c$—OH or $R_d$—OH) is reacted with a compound (a) to obtain a compound (b). The reaction can be conducted by means of the method of dehydration/condensation reaction using an acid catalyst, the activation of esterification method, the acid anhydride method, the mixed anhydride method, the halogenation of carboxylic acid method, the carboxylic acid azide method, etc. Among them, dehydration/condensation using an acid catalyst is preferred since it can be conducted most conveniently and purification can also be easily conducted in this case. A dehydration/condensation reaction can be conducted according to the ordinary method. However, since heating is required in the case of dehydration/condensation using an acid catalyst, when a raw material is unstable against heat, another method is preferably selected. In order to cause a reaction of interest at a site of interest, according to need, a reactive functional group of the compound (a) is preferably protected with a protective group such as a tert-butoxy group, a tert-butoxycarbonyl group and a benzyloxycarbonyl group in advance.

Next, a compound (c) is reacted with the compound (b) obtained above to obtain a compound (d). It is desired that an amino group of the compound (c) is protected with a tert-butoxy group, a tert-butoxycarbonyl group, a benzyloxycarbonyl group or the like in advance, and that a carboxyl group of the compound (c) is activated by N-hydroxysuccinimide or the like in advance. In the next step, when compounds (e) and (e') are different from each other, 2 amino groups of the compound (c) are preferably protected with protective groups whose reactivities are different from each other, respectively, in advance. For example, when one amino group is protected with a tert-butoxycarbonyl group and the other amino group is protected with a benzyloxycarbonyl group, in the next step, the compound (e) or (e') can be selectively reacted with any of the amino groups of the compound (c). The reaction can be conducted by means of the activation of esterification method, the acid anhydride method, the mixed anhydride method or the like. Further, solid-phase synthesis may be conducted in a manner similar to that of usual peptide synthesis. Note that the reaction is preferably conducted in the presence of a catalyst such as tertiary amine.

After the completion of the reactions, deprotection is conducted by a treatment with an acid such as trifluoroacetic acid, and purification is conducted according to the ordinary method, thereby obtaining the compound (d). The termination point of the reactions can be confirmed by gas chromatography, high performance liquid chromatography, thin layer chromatography, nuclear magnetic resonance spectroscopy, infrared absorption spectroscopy or the like.

Next, the compounds (e) and (e') are reacted with the amino groups of the obtained compound (d). In the compounds (e) and (e'), it is desired that the amino groups are protected with a tert-butoxy group or the like in advance, and that one carboxyl group is protected with a tert-butoxy group and the other carboxyl group is activated using N-hydroxysuccinimide or the like in advance. The reaction can be conducted by means of the activation of esterification method, the acid anhydride method, the mixed anhydride method, etc. Further, solid-phase synthesis may be conducted in a manner similar to that of usual peptide synthesis. The reaction is preferably conducted in the presence of a catalyst such as tertiary amine.

After the completion of the reaction, deprotection is conducted in the same manner as described above, and purification is conducted according to the ordinary method, thereby obtaining a compound (f). The termination point of the reactions can be confirmed in the same manner as described above.

The above-described reactions can be performed at room temperature. Further, the reactions can be performed either under elevated pressure, reduced pressure or atmospheric pressure, but is preferably performed under atmospheric pressure because the operation is simple.

The amphiphilic molecule of the present invention can be produced in the above-described way. According to a preferred embodiment of the present invention, by using the amphiphilic molecule of the present invention as a constituent of the molecular assembly, a vesicular structure in which the zeta potential is neutral or negative is formed under physiological conditions to carry a substance of interest, and when the zeta potential becomes positive under acidic conditions, by the interaction with an anionic biomembrane, the vesicular structure is deformed, thereby releasing the substance of interest to the outside of the vesicular structure.

The structure of the amphiphilic molecule of the present invention is not limited to those described above as long as the amphiphilic molecule has the cationic functional group and the anionic functional group in its hydrophilic moiety, thereby constituting the molecular assembly having the above-described properties. It should be understood that all compounds, which are obtained by design change or the like based on the technical idea of the present invention, and which provide the above-described functions, are included in the scope of the present invention.

[2] Molecular Assembly

The molecular assembly of the present invention includes the aforementioned amphiphilic molecule of the present invention as its constituent. In this regard, the "molecular assembly" refers to an assembled product of molecules having a specific form, which is formed when the amphiphilic molecule of the present invention is dispersed in a water-based medium together with, according to need, steroids and other amphiphilic molecules.

According to a preferred embodiment of the present invention, the molecular assembly of the present invention includes the amphiphilic molecule of the present invention as its constituent, and therefore, can exhibit pH responsiveness. That is, in an aqueous solution, a vesicular structure in which the zeta potential is neutral or negative is formed under a physiological pH environment, but under an acidic pH environment, ionization tendency of the anionic functional group in the amphiphilic molecule of the present invention is diminished, and since the net electric charge of the molecular assembly becomes cationic, the zeta potential becomes positive, and accordingly, interaction with an anionic biomembrane becomes easier. More preferably, the molecular assembly of the present invention forms a vesicular structure in which the zeta potential is neutral or negative under a physiological pH environment to carry a substance of interest, and when the zeta potential becomes positive under an acidic pH environment, by interaction with an anionic biomembrane, the vesicular structure is changed, thereby releasing the substance of interest to the outside of the vesicle.

The pH range in which the zeta potential of the molecular assembly of the present invention changes from negative to positive is not particularly limited. The pH range in which the zeta potential of the molecular assembly of the present invention changes from negative to positive can be adjusted by the type of amphiphilic molecule to be used, combination with other constituents and its blend ratio, etc., and can be suitably selected depending on purposes, application, etc. The pH range in which the zeta potential of the molecular assembly of the present invention changes from negative to positive is preferably 4.0 or higher, more preferably 4.5 or higher, even more preferably 5.0 or higher, and particularly preferably 5.5 or higher. Further, the pH is preferably lower than 7.2, more preferably lower than 7.0, even more preferably lower than 6.5, still more preferably lower than 6.0, and particularly preferably 5.5 or lower. This specification discloses ranges provided by free combinations of these upper and lower limits.

In one embodiment of the present invention, the zeta potential of the molecular assembly of the present invention can change from negative to positive at pH of 4.0 to 6.0, which is typical in the environment of an endosome. Therefore, it is thought that the molecular assembly has high ability to release a substance of interest, which is carried out by means of endosomal membrane fusion, to the cytoplasm side at the time of being taken into a target cell.

It is thought that such behavior of the molecular assembly of the present invention occurs when the charge balance of the hydrophilic moiety of the amphiphilic molecule is changed in response to pH of an aqueous solution and it affects the molecular packing state of molecular assembly, leading to change of the structure of the molecular assembly. According to a preferred embodiment of the present invention, by utilizing the above-described property of the molecular assembly of the present invention, a substance of interest can be efficiently delivered to a target affected area. In addition, according to a preferred embodiment of the present invention, the molecular assembly of the present invention can release a substance of interest to the outside of an endosome that is an anionic biomembrane in a cell, into cytoplasm, when taken into the endosome.

Hereinafter, release behavior of the molecular assembly of the present invention will be described with reference to the drawings. FIG. 1 is a schematic view showing behavior of the molecular assembly of the present invention in which it is taken into a target cell and then releases a substance of interest carried by it.

Firstly, before taken into a cell, the molecular assembly of the present invention retains a vesicular structure of the molecular assembly under a physiological pH environment and stably carries an inclusion (FIG. 1(a)). Under a physiological pH environment, the zeta potential of the molecular assembly is neutral or negative. Therefore, for example, when administered into the blood, adsorption to a blood vessel wall or the like, whose surface potential is negative at the time of retention in the blood, is avoided, and accordingly good retention property in the blood is exerted. This molecular assembly moves toward a cell membrane while circulating through a living body and is taken into a cell by endocytosis (FIG. 1(b)).

In the molecular assembly taken into the cell by endocytosis, the zeta potential changes from neutral or negative to positive under an acidic pH environment in endosome, and in an endosome membrane, which is rich in negatively charged lipid, the zeta potential is negative. Therefore, adsorption to the endosome membrane is promoted. Further, by interaction (preferably fusion) with the endosome membrane, the vesicular structure of the molecular assembly is changed. This enables the molecular assembly to release the substance of interest carried to the outside of the endosome (FIG. 1(c)).

According to a preferred embodiment of the present invention, the molecular assembly of the present invention can deliver a substance of interest under a pH environment which is similar to the environment in endosome. Therefore, a larger amount of substance of interest can be delivered into cytoplasm in a short time.

Usually, a foreign substance is taken into a cell by endocytosis, and then digested in a lysosome containing degradative enzymes. On the other hand, in the case of the molecular assembly of the present invention, since a substance of interest is carried by the molecular assembly, the substance of interest can be efficiently delivered into a cell or nucleus before degraded in lysosome. Note that FIG. 1 shows one example among many, and the form of the molecular assembly, the method of carrying a substance of interest, behavior of releasing a substance of interest, etc. are not limited thereto.

With respect to the amphiphilic molecule of the present invention in the molecular assembly of the present invention, one type of amphiphilic molecule can be used, or two or more types of amphiphilic molecules can be used in combination. The content of the amphiphilic molecule in the molecular assembly of the present invention is preferably 10 to 100 mol %, more preferably 20 to 80 mol %, and even more preferably 30 to 60 mol % based on the total molarity of the constituents in the molecular assembly. The higher the content of the amphiphilic molecule of the present invention is, the higher the release kinetics or the release rate of a substance of interest is. The content of the amphiphilic molecule of the present invention can be suitably adjusted depending on an area in the body into which a substance of interest is desired to be introduced, a desired release rate or release kinetics, etc.

Moreover, in addition to the amphiphilic molecule of the present invention, the molecular assembly of the present invention may include other constituents. For example, the molecular assembly of the present invention may include steroids. Examples of steroids include all steroids having perhydrocyclopentanophenanthrene, such as sterols, bile acid, provitamin D, and steroid hormone. Among them, sterols are preferably used. Examples of sterols include ergosterol and cholesterol. Among them, cholesterol is preferably used.

The content of steroids to be used in the molecular assembly of the present invention is not particularly limited, but is preferably 10 to 60 mol %, and more preferably 20 to 50 mol % based on the total molarity of the constituents in the molecular assembly. Since steroids can act as a stabilizer for the molecular assembly, the content thereof may be suitably adjusted depending on a desired release kinetics, release rate and the like. These steroids can be used solely or in combination.

In addition, the molecular assembly of the present invention may include at least one ionic lipid component selected from the group consisting of zwitterionic lipids, cationic lipids and anionic lipids other than the amphiphilic molecule of the present invention without departing from the purpose of the present invention and in particular, within the range in which retention property in the blood is not adversely affected when the molecular assembly of the present invention is administered into the blood.

These ionic lipids can be used solely or in combination. The content of these lipids is not particularly limited, but is preferably 0 to 90 mol %, and more preferably 0 to 50 mol % based on the total molarity of the constituents in the molecular assembly. However, since these cationic lipids tend to be easily adsorbed to a blood vessel wall or the like at the time of retention in blood, there is a case where the retention property in the blood of the molecular assembly is decreased. Therefore, the amount of the cationic lipids to be used is preferably about 0 to 50 mol % based on the total molarity of the constituents in the molecular assembly.

The molecular assembly of the present invention may further comprise polyethylene glycol-type lipid. By using polyethylene glycol-type lipid as a constituent, aggregation of the molecular assembly is suppressed, thereby increasing retention time in the blood after administered into a living body. In this case, one type of polyethylene glycol-type lipid can be used, or two or more types of polyethylene glycol-type lipids can be used in combination. The content of these polyethylene glycol-type lipids is not particularly limited, but is preferably 0 to 30 mol %, and more preferably 0.1 to 0.5 mol % based on the total molarity of the constituents in the molecular assembly. The molecular weight of a polyethylene glycol moiety of the polyethylene glycol-type lipid that can be used in the present invention is not particularly limited, but is preferably about 200 to 50,000, and more preferably about 5,000 to 20,000.

In addition, the molecular assembly of the present invention may include one or more types of phospholipids known as constituents of a molecular assembly such as egg-yolk lecithin, soybean lecithin, hydrogenated egg-yolk lecithin, hydrogenated soybean lecithin, phosphatidylcholines, phosphatidylglycerols, phosphatidylethanolamines, sphingomyelin and various types of glycolipids. The content of these lipids is not particularly limited, but is preferably 0 to 80 mol %, and more preferably 40 to 70 mol % based on the total molarity of the constituents in the molecular assembly.

According to a preferred embodiment of the present invention, the molecular assembly of the present invention carries a substance of interest. In this regard, the expression "the molecular assembly carries a substance of interest" refers to a state in which the substance of interest interacts with a hydrophilic region (aqueous phase) in the molecular assembly or the inside of a lipid bilayer membrane or the outer surface of a molecular membrane. Examples of such states include: (i) a state in which a water-soluble or hydrophobic substance of interest is localized in the aqueous phase in the molecular assembly; (ii) a state in which a complex in which a water-soluble or hydrophobic substance of interest is included in a hydrophilic polymer is localized in the aqueous phase in the molecular assembly; and (iii) a state in which a hydrophobic substance of interest is localized in a hydrophobic region in a bilayer membrane or to the outer surface of a bilayer membrane.

The substance of interest to be used in the molecular assembly of the present invention is not particularly limited as long as it can be carried by the molecular assembly of the present invention. The substance of interest preferably acts on at least one of organ, tissue and cell to be targeted. For example, the substance of interest is preferably at least one type of substance selected from the group consisting of drugs, probes, nucleic acids (including given DNA, RNA, siRNA, etc.), proteins, peptides, metal ions (including given lithium ion, sodium ion, magnesium ion, calcium ion, iron ion, copper ion, etc.) and metal complexes (including given iron complex, copper complex, platinum complex, gadolinium complex, vanadium complex, zinc complex, manganese complex, etc.). According to a preferred embodiment of the present invention, these substances carried by the molecular assembly of the present invention are taken into an endosome in a cell by endocytosis, and then released into cytoplasm, thereby being efficiently delivered into a cell. The molecular weight of the substance of interest carried by the molecular assembly of the present invention is usually 5 to 1,000,000, preferably 30 to 1,000,000, more preferably 200 to 500,000, and even more preferably 300 to 100,000.

Examples of the substance of interest to be used in the present invention include enzymes, peptides or proteins, antibodies (including single-chain antibodies), receptors, ligands, various antibiotics, various peptide hormones, DNAs, RNAs, siRNAs, plasmids, probes, various anticancer agents, agents for the central nervous system, agents for peripheral nerve, agents for sense organ, agents for organ of circulation, agents for respiratory organ, agents for digestive organ, hormonal agents, agents for urinary organs, reproductive organs and anus, agents for skin, agents for dental and oral use, vitamin preparation, revitalizer, agents for blood and body fluid, agents for hemodialysis, other metabolic agents, cellular stimulants, agents for tumors, radioactive agents, agents for allergy, pharmaceutical agents based on crude drugs and Chinese medicine formulations, antibiotics preparations, chemotherapeutic agents, biological preparations, and diagnostic agents. Examples of peptides or proteins include antibodies, receptors, ligands, various cytokines (e.g., interleukin), cell communication factors, cell growth factors, fibrinogen, collagen, keratin, polypeptides as agents for extracellular matrix such as proteoglycan or oligo bodies as portions thereof, and functional polypeptides such as oxytocin, bradykinin, thyrotropin-releasing factor and enkephalin. Examples of enzymes include catalase, chymotrypsin, cytochrome and amylase, but the present invention is not limited thereto. Examples of probes include antibodies, antigens, pigments, various types of labeling substances such as fluorescent pigments and active substances. These substances can be used solely or in combination.

The content of the substance of interest to be carried by the molecular assembly of the present invention significantly varies depending on the type, purpose, etc. of the substance of interest, but is preferably 0.001 to 1000 wt %, more preferably 0.01 to 200 wt %, and even more preferably 0.1 to 50 wt % based on the total weight of the constituents in the molecular assembly (however, excluding the weight of the substance of interest).

The form of the molecular assembly of the present invention is not particularly limited. Examples thereof include polymer assemblies (e.g., a polymer complex, a polymer micelle and a polymer-liposome), emulsions, lipid microspheres, bilayer membrane vesicles (liposome), and other molecular assemblies (e.g., a tube, fiber, ribbon, and sheet). Among them, liposome is preferred.

In the case where the molecular assembly of the present invention is a liposome, when the liposome is dispersed in an aqueous medium, the liposome can include an internal aqueous phase. In this case, it is preferred that the substance of interest carried by the molecular assembly is dissolved or dispersed in the internal aqueous phase of the liposome. Alternatively, the substance of interest may be localized in a bilayer membrane (for example, the substance of interest may be held in a hydrophobic region of the liposome bilayer membrane).

When the content of the constituents in the molecular assembly is referred to herein, the internal aqueous phase is not taken into consideration.

The particle size of the molecular assembly of the present invention is preferably 25 to 10,000 nm, more preferably 100 to 500 nm, and even more preferably 150 to 300 nm.

The method for producing the molecular assembly of the present invention is not particularly limited. The molecular assembly of the present invention can be produced according to a publicly-known method. For example, as a method for producing a liposome, the following methods can be employed: a method in which powder or a thin film of single or mixed lipid is hydrated and dissolved, and thereafter a molecular assembly is produced using the high-pressure extrusion method, an ultrasonic irradiation method, a stirring method (e.g., vortex mixing and homogenizer), a high-speed stirring method, a French press method, a freeze-thawing method, a microfluidization method or the like; a method in which a solution in which a single or mixed lipid is dissolved in an organic solvent is injected into an aqueous phase, and thereafter the organic solvent such as ethanol and ether is removed by pressure reduction or dialysis, thereby forming a molecular assembly; a method in which a single or mixed lipid is dispersed into an aqueous phase together with a non-ionic surfactant such as sodium cholate, sodium dodecyl sulfate, Triton X-100, octyl glycoside and lauryl ether to form an emulsion, and thereafter removal is performed by dialysis, thereby forming a molecular assembly; a reverse phase evaporation method; and an incubation method.

The method for getting the substance of interest to be carried by the molecular assembly of the present invention may be suitably selected depending on the type, etc. of the substance of interest. For example, in the case where the substance of interest is a water-soluble drug, it can be encapsulated in the molecular assembly (e.g., in an internal aqueous phase of a liposome) at the time of production of the molecular assembly, wherein the drug is dissolved in an aqueous phase and the molecular assembly is formed using the aforementioned method. Alternatively, in the case where the substance of interest is a water-soluble drug having membrane permeability, after forming the molecular assembly (liposome), the drug is dissolved in an outer aqueous phase, and then the drug can be encapsulated in an inner aqueous phase utilizing membrane permeability. The water-soluble substance that was not encapsulated can be separated from an encapsulating vesicle by means of gel filtration, ultracentrifugal separation, treatment with ultrafiltration membrane or the like.

Alternatively, in the case where the substance of interest is a lipid-soluble or amphiphilic drug, the drug is mixed with an organic solvent in which a single or mixed lipid is dissolved, and the molecular assembly is formed using the aforementioned method, thereby getting the drug to be carried by the hydrophobic moiety in the molecular assembly (e.g., the inside of a bilayer membrane of liposome). Alternatively, after preparing a fluid dispersion of the molecular assembly using the aforementioned method, a solution in which the drug is dissolved in a solvent that is miscible with water (e.g., ethanol and DMSO) is added thereto, thereby the drug can be carried by the hydrophobic moiety.

In the case where the substance of interest is a probe, nucleic acid or protein, the substance of interest can be carried by the molecular assembly using the same method as described above or can be carried by localizing onto the outer surface of molecular assembly.

[3] Application of the Molecular Assembly (1) Agents

For example, when the molecular assembly of the present invention carries a drug, the molecular assembly of the present invention can be used as an agent. The content of the drug can be suitably determined depending on the type or purpose of the drug, but is preferably 0.001 to 1000 wt %, more preferably 0.01 to 100 wt %, and even more preferably 0.1 to 10 wt % based on the total weight of the constituents in the molecular assembly (however, excluding the weight of the substance of interest). The method for administering the agent of the present invention is not particularly limited. For example, the agent of the present invention can be administered orally, parenterally, intravenously, buccally, rectally, vaginally, transdermally, or via nasal passage or inhalation. Moreover, the agent can be directly administered (locally administered) to a diseased site. The agent of the present invention is sufficient when it is within the range of effective amount. The dose varies depending on a target disease, a target to be administered, an administration method, symptoms, etc., but the daily dose is usually about 0.001 to 1400 mg/kg body weight (the weight of the constituent (lipid) of the molecular assembly).

Examples of drugs to be carried by the molecular assembly of the present invention include various anticancer agents, agents for the central nervous system, agents for peripheral nerve, agents for sense organ, agents for organ of circulation, agents for respiratory organ, agents for digestive organ, hormonal agents, agents for urinary organs, reproductive organs and anus, agents for skin, agents for dental and oral use, vitamin preparation, revitalizer, agents for blood and body fluid, agents for hemodialysis, other metabolic agents, cellular stimulants, agents for tumors, radioactive agents, agents for allergy, pharmaceutical agents based on crude drugs and Chinese medicine formulations, antibiotics preparations, chemotherapeutic agents, and biological preparations.

(2) Reagents, Diagnostic Agents and Kits

Further, when the molecular assembly of the present invention carries a probe, antibody or nucleic acid, the molecular assembly of the present invention can be used as a reagent or diagnostic agent. For example, when the molecular assembly of the present invention carries a probe, the molecular assembly of the present invention is useful as a reagent/diagnostic agent for detection of biological substances such as genes or a reagent for diagnosis of localization or function of intracellular substances.

The probe to be used in the present invention is not particularly limited as long as it is a molecule for detecting a specific substance, site, state or the like of a gene, gene product or the like. Examples of probes include antibodies, antigens, pigments, various types of labeling substances such as fluorescent pigments and active substances. Among them, as biologically active substances (substances which act on living bodies), for example, nucleic acids, proteins, and other small molecules are included. For example, when a fluorescent pigment is carried as a probe, the reagent of the present invention can be used, for example, at the time of detecting a site of liposome localization in a living body.

The content of the probe to be carried by the molecular assembly of the present invention can be suitably determined depending on the type or purpose of the probe, but is preferably 0.001 to 1000 wt %, more preferably 0.01 to 100 wt %, and even more preferably 0.1 to 10 wt % based on the total weight of the constituents in the molecular assembly (however, excluding the weight of the substance of interest).

Further, for example, when the molecular assembly of the present invention carries a nucleic acid, the molecular assembly of the present invention is useful as a nucleic acid-introducing agent. A nucleic acid-introducing agent comprising the molecular assembly of the present invention is not digested by a lysosome and can efficiently deliver a gene of interest into cytoplasm or cell nucleus. Therefore, the agent is useful for gene therapy and the like.

For example, when the molecular assembly of the present invention carries a nucleic acid which controls gene expression of decoy DNA, siRNA, antisense DNA or the like, the molecular assembly is useful as a reagent for promoting knockdown of a specific gene, etc.

When using the reagent of the present invention for gene therapy, for example, the reagent can be administered orally, parenterally, intravenously, buccally, rectally, vaginally, transdermally, or via nasal passage or inhalation. Moreover, the reagent can be directly administered to a diseased site in a living body.

When the reagent of the present invention is used for nucleic acid introduction, the amount thereof to be used is about 0.001 to 100 µmol, and preferably about 0.1 to 10 µmol per $1 \times 10^4$ cells (the molarity of the constituent (lipid) of the molecular assembly), but may be suitably set based on the amount to be used of a liposome reagent or the like in which a cationic lipid (e.g., Lipofectamine, Transome, DOTAP, and DMRIE), which has been conventionally used as a gene introducing reagent, is used as a constituent lipid. When employing this amount, an introduction efficiency that is nearly equal to that of a conventional gene introducing reagent (Lipofectamine) can be obtained without cytotoxicity.

The present invention also provides a kit for detection of biological substances, diagnosis of localization or function of intracellular substances or gene therapy, which comprises the above-described reagent or diagnostic agent. In the kit of the present invention, a buffer solution, a pH adjuster, a cell protective solution, etc. may be included solely or in suitable combination. According to need, the kit may include a reference nucleic acid which is used as the control of transfection. Examples of such nucleic acids include those encoding reporter or marker proteins (e.g., luciferase, β-galactosidase, and GFP). The nucleic acid may be in the form of a plasmid vector. According to need, the kit of the present invention can also include, for example, a transfection enhancement reagent (e.g., DEAE dextran) and other additives. The kit of the present invention can also include instruction for detecting a specific substance, site, state or the like of a gene, gene product or the like, or instruction for introducing a nucleic acid. Each component to be included in the kit may be, for example, in the packaged state in which each component is included in a container.

(3) Protein Preparations for Enzyme Replacement Therapy

When the molecular assembly of the present invention carries a protein, the molecular assembly of the present invention can be used as a preparation for enzyme replacement therapy. Examples of proteins include adenosine deaminase, nitric oxide synthetase, superoxide dismutase, arginosuccinic acid synthetase, phenylalanine hydroxylase, α-galactosidase and β-glucosidase. The preparation for enzyme replacement therapy of the present invention can be used, for example, for a patient with a symptom in which a specific enzyme is not expressed or expressed insufficiently. The content of the protein can be suitably determined depending on the type or purpose, but is preferably 0.001 to 1000 wt %, more preferably 0.01 to 200 wt %, and even more preferably 0.1 to 50 wt % based on the total weight of the constituents in the molecular assembly (however, excluding the weight of the substance of interest). The method for administering the preparation is not particularly limited. For example, the preparation can be administered orally, parenterally, intravenously, buccally, rectally, vaginally, transdermally, or via nasal passage or inhalation. The dose of the preparation is sufficient when it is within the range of effective amount, and the dose varies depending on a target disease, a target to be administered, an administration method, symptoms, etc. However, the amount to be used per day is usually about 0.001 to 1400 mg/kg body weight (the weight of the constituent (lipid) of the molecular assembly).

EXAMPLES

Hereinafter, the present invention will be specifically described by way of illustrative examples, but the present invention is not limited thereto.

Example 1

Synthesis of pH-Responsive Amphiphilic Molecule (GGLG: Ia-1)

Step (A): A benzene solution (100 mL) of p-toluenesulfonic acid monohydrate (4.56 g, 24 mmol) was subjected to boiling point reflux at 85° C., and water was removed before the reaction using Dean-Stark apparatus. Glutamic acid (2.96 g, 20 mmol) and hexadecylalcohol (10.7 g, 44 mmol) were added to the reaction solution, and the mixture was subjected to boiling point reflux for 10 hours while the generated water was removed. As the reaction proceeded, the suspension was gradually dissolved to become transparent.

After the reaction completed, the solvent was removed under reduced pressure. The resultant solution was dissolved in chloroform, and washed with a saturated aqueous solution of sodium carbonate 3 times. The chloroform layer was dehydrated with magnesium sulfate. The resultant substance was filtered, and then the solvent was removed under reduced pressure. The residue was recrystallized with methanol at 4° C. to obtain Compound 1 (yield: 83%) as white powder.

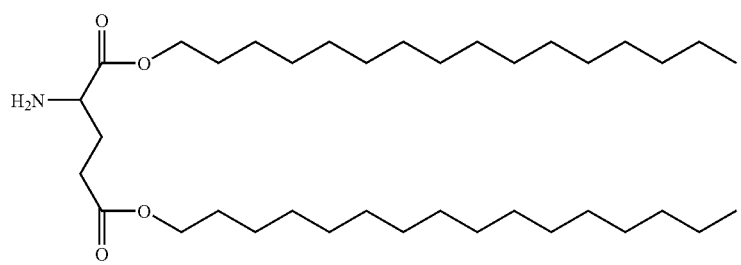

Compound 1

(1) The analytical results of Compound 1 were as follows:
Thin layer chromatography (silica gel plate, chloroform/methanol (4/1) (volume/volume): $R_f$: 0.83 (monospot))
Infrared absorption spectrum (cm$^{-1}$): 1737 ($v_{C=O}$, ester).

$^1$H-NMR (CDCl$_3$, 500 MHz, δ ppm): 0.88 (t, 6H, —CH$_3$); 1.25 (br, 52H, alkyl); 1.62 (m, 4H, —CO—O—C—CH$_2$—); 1.84 (m, 1H, glu β-CH$_2$—); 2.08 (m, 1H, glu β-CH$_2$—); 2.45 (t, 2H, glu γ-CH$_2$—); 3.45 (t, 1H, glu α-CH—); 4.06, 4.12 (t, 4H, —CO—O—CH$_2$—)

MS (ESI) Calcd: 595.9; Found: 597.3 (MH)$^+$.

Step (B): Compound 1 obtained in step (A) (1.0 g, 1.67 mmol) and triethylamine (202 mg, 2.0 mmol) were dissolved in 30 mL of dichloromethane and stirred at room temperature for 1 hour. Then, lysine (617 mg, 1.4 mmol), in which an amino group was protected by a t-butoxy group and a carboxyl group was activated by N-hydroxysuccinimide, was added thereto, and stirred at room temperature for another 6 hours.

After the reaction completed, the solvent was removed under reduced pressure. The resultant solution was dissolved in chloroform, and washed with a saturated aqueous solution of sodium carbonate 3 times. The chloroform layer was dehydrated with magnesium sulfate. The resultant substance was filtered, and the solvent was removed under reduced pressure. The residue was recrystallized with methanol at 4° C. and filtered with a glass filter (G6) to obtain a lysine derivative having a protected amino group.

Trifluoroacetic acid (20 mL) was added to the resultant derivative and stirred at 4° C. for 2 hours. After the reaction completed, the solvent was removed under reduced pressure. The resultant solution was dissolved in chloroform, and washed with a saturated aqueous solution of sodium carbonate 4 times. The chloroform layer was dehydrated with magnesium sulfate. The resultant substance was filtered, and the solvent was removed under reduced pressure. The residue was recrystallized with methanol at 4° C., filtered and dried to obtain Compound 2 (80%) as white powder.

The analytical results of Compound 2 were as follows:

(2): Thin layer chromatography (silica gel, chloroform/methanol (4/1) (volume/volume): $R_f$: 0.63 (monospot))
Infrared absorption spectrum (cm$^{-1}$): 1737 ($v_{C=O}$, ester); 1673 ($v_{C=O}$, amide) $^1$H-NMR (CDCl$_3$, 500 MHz, δ (ppm)): 0.83 (t, 6H, —CH$_3$); 1.19 (br, 52H, —CH$_2$—); 4.33 (d, 1H, glu α-CH—); 4.50 (br, 1H, lys α-CH—); 7.8, 8.2 (br, 2H, —NH$_2$)

Step (C): Compound 2 obtained in step (B) (500 mg, 691 mmol) and triethylamine (107 μl, 829 mmol) were dissolved in 30 mL of dichloromethane and stirred at room temperature for 1 hour. Then, glutamic acid (639 mg, 1.45 mmol), in which an amino group and a γ-carboxyl group were protected by a t-butoxy group and a t-butylester group, respectively, and an α-carboxyl group was activated by N-hydroxysuccinimide, was added thereto, and stirred at room temperature for another 6 hours.

After the reaction completed, the solvent was removed under reduced pressure. The resultant solution was dissolved in chloroform, and washed with a saturated aqueous solution of sodium carbonate 3 times. The chloroform layer was dehydrated with magnesium sulfate. The resultant substance was filtered, and the solvent was removed under reduced pressure. The residue was recrystallized with methanol at 4° C. and filtered with a glass filter (G6) to obtain a lysine derivative having a protected amino group.

Trifluoroacetic acid (20 mL) was added to the resultant lysine derivative and stirred at 4° C. for 2 hours. After the reaction completed, the solvent was removed under reduced pressure. The resultant solution was dissolved in chloroform, and washed with a saturated aqueous solution of sodium carbonate twice. The chloroform layer was dehydrated with magnesium sulfate. The resultant substance was filtered, and the solvent was dried under reduced pressure, thereby obtaining Compound 3, the amphiphilic molecule of the present invention (GGLG: Ia-1) (65%), as white powder.

Compound 2

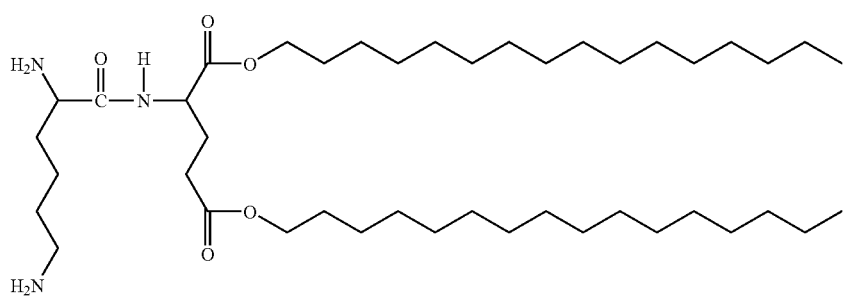

Compound 3

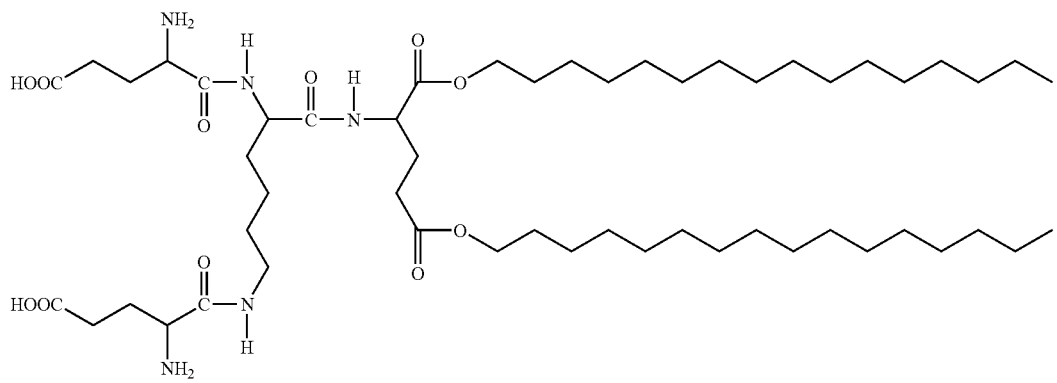

The analytical results of Compound 3 were as follows: (3): Thin layer chromatography (silica gel, chloroform/methanol (4/1) (volume/volume): $R_f$: 0.05 (monospot))
Infrared absorption spectrum (cm$^{-1}$): 1737 ($v_{C=O}$, ester); 1673 ($v_{C=O}$, amide)
$^1$H-NMR (CDCl$_3$, 500 MHz, δ (ppm)): 0.84 (t, 6H, —CH$_3$); 1.23 (br, 52H, alkyl); 3.88, 3.93 (t, 1H, glu α-CH-Lys-); 4.34 (q, 1H, lys α-CH—); 4.44 (q, 1H, glu α-CH—COO—)

The synthesized amphiphilic molecule of the present invention can be synthesized in 3 steps, and purification thereof can be performed only by means of recrystallization. Therefore, there is an advantage in that a large amount of the amphiphilic molecule of the present invention can be synthesized in a high yield (higher than 40%) in a short time using a convenient method. This is significantly more advantageous compared to the phospholipid derivatives such as DOPE which have been reported.

Example 2

Preparation of Liposome

Compound 3 (174 mg, 0.177 mmol), cholesterol (69.3 mg, 0.179 mmol) and N-methoxypolyethylene glyco-1,5-diocta-decyl-L-glutamate (PEG-Glu2C$_{18}$: PEG, Mw 5000) (6.0 mg, 1.0 μmol) were dissolved in benzene, and the mixture was freeze-dried to prepare a mixed lipid. 20 mg of this mixed lipid was dispersed in 1 mL of water for injection, and the resultant mixture was stirred for 6 hours. After that, liposome having a particle size of about 225 nm (hereinafter sometimes referred to as "pH-responsive liposome") was prepared by means of the high-pressure extrusion method (final pore diameter: 0.22 μm).

<Measurement of Zeta Potential>

Portions of the prepared liposome ([lipid]=10 mg/ml) were respectively added to acetate buffers with different pHs (7.4, 7, 6, 5, 4) (30 mM) to the final concentration of [lipid]=1 mg/mL, and then the zeta potential at 37° C. was measured. Zetasizer 4 manufactured by Malvern was used. A capillary cell was filled with a liposome-dispersed liquid obtained by dilution to the measurement concentration, and the measurement was performed at 37° C. 3 times. The results are shown in FIG. 2.

Figure 2:
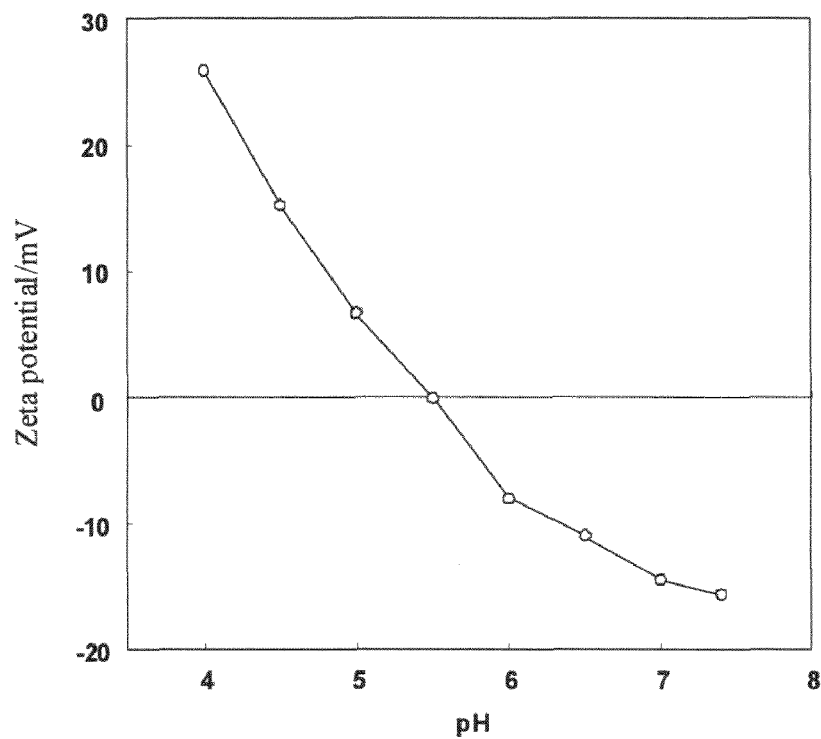
FIG. 2 is a graph showing measurement results of the zeta potential of a liposome comprising Compound 3 as a membrane component.

As understood from FIG. 2, in the case of the liposome comprising Compound 3 as its constituent, as pH was decreased, the zeta potential was increased and changed from negative to positive. It is thought that this is because the zeta potential of the liposome is negative at pH 7.4 and a carboxyl group at the γ-position of the hydrophilic moiety projects through the surface more than an amino group. That is, it is thought that the zeta potential became positive as pH was decreased (pH 5 to 6) because the state of the carboxyl group of glutamic acid changed from a dissociative state to a non-dissociative state. In FIG. 2, (○) shows change in the zeta potential of Compound 3/cholesterol/PEG-Glu2C18 (5/5/0.03 (molar ratio)).

<Examination 1 Regarding Interaction with Anionic Biomembrane>

It is known that an endosome membrane is rich in anionic lipids such as phosphatidylserine (PS) and phosphatidylglycerol (PG). Therefore, in order to elucidate the adsorption action to anionic biomembranes for behavior analysis of a pH-responsive liposome in an endosome, aggregation degrees (including fusion) of an anionic liposome (c.a. 250 nm) and a pH-responsive liposome (c.a. 250 nm) were measured with different pHs and different particle sizes.

Figure 3:
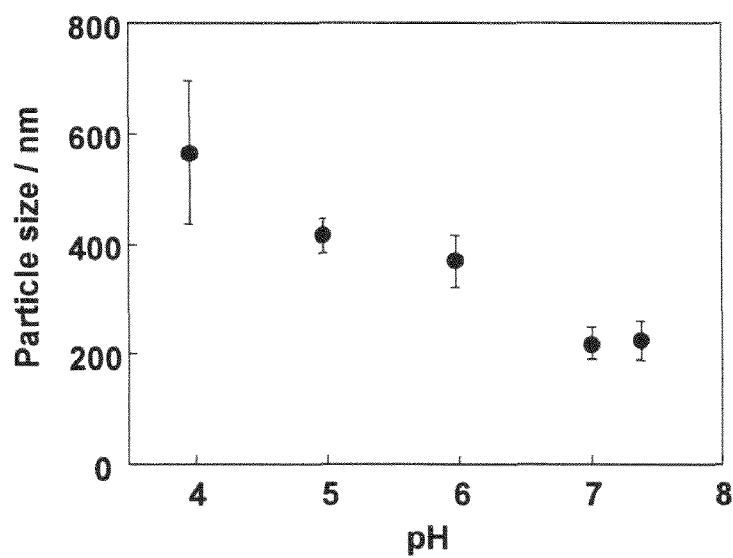
FIG. 3 is a graph showing change in the aggregation degree of a pH-responsive liposome and an anionic liposome depending on pH.

Each of an anionic liposome (dipalmitoylphosphatidylcholine (DPPC)/cholesterol/dipalmitoylphosphatidylglycerol (DPPG)=4/5/1 (molar ratio), [lipid]=1 mg/ml) and a pH-responsive liposome=1 mg/ml) (each 50 μL) was added to 30 mM acetate buffer, and the particle size was measured using a light scattering photometer. N4 PLUS Submicron Particle Size Analyzer manufactured by Beckman was used. A cell was filled with 2 mL of a liposome-dispersed liquid obtained by dilution to the measurement concentration, and the apparent particle size was measured 3 times using the dynamic light scattering method. The results are shown in FIG. 3. FIG. 3 shows aggregation degrees at different. pHs (4, 5, 6, 7, 7.4) (n=3).

As understood from FIG. 3, the particle size of the anionic liposome or pH-responsive liposome was constant regardless of pH values. However, when the pH-responsive liposome was mixed with the anionic liposome, the particle size increased as pH of the dispersion medium decreased. At pH 6, the particle size of the pH-responsive liposome became about 400 nm, and as pH decreased, the particle size increased. At pH 4, the particle size became about 650 nm. This means aggregation between liposomes. The aggregation degree increased as the zeta potential of the pH-responsive liposome increased to more positive values. This suggests that the pH-responsive liposome has properties required for promoting aggregation and fusion with an endosome membrane under a pH environment in endosome.

<Examination 2 Regarding Interaction with Anionic Biomembrane>

In addition, the degree of membrane fusion of a pH-responsive liposome with an anionic biomembrane as a hypothetical endosome membrane under a pH environment in endosome was measured by the dilution method utilizing FRET (fluorescence resonance energy transfer).

Figure 4:
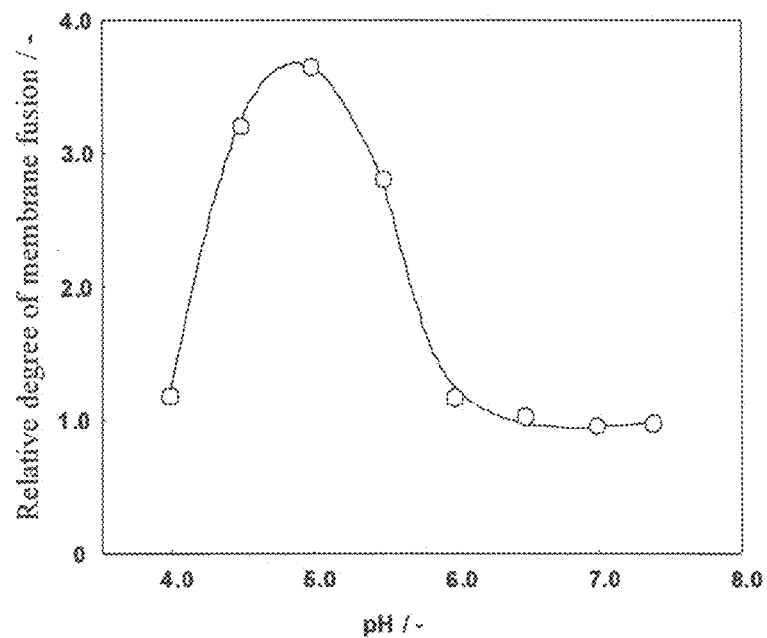
FIG. 4 is a graph showing the relative degree of membrane fusion of a pH-responsive liposome and an anionic liposome at each pH.

As a hypothetical endosome, an anionic liposome comprising dioleoylphosphatidylcholine (DOPC)/cholesterol/dioleoylphosphatidylserine (DOPS)/1,2-Dioleoyl-sn-glycero-3-phosphoethanolamine-N-(7-nitro-2-1,3-benzoxadiazol-4-yl) (NBD-PE)/1,2-dioleoyl-sn-glycero-3-phosphoethanolamine-N-(lissamine rhodamine B sulfonyl) (R-PE) (=3/1/0.3/0.0022/0.0022, molar ratio) as its constituent was prepared. Firstly, 25 μl of 500 μM anionic liposome and 25 μl of 4.5 mM pH-responsive liposome (Compound 3/cholesterol/PEG-Glu2C$_{18}$=5/5/0.03, molar ratio) were added to 200 μl of each of acetate buffers with different pHs, and incubation was carried out (37° C., 30 min). Subsequently, 20 μl of each of the mixtures was added to 80 μl of 150 mM saline, and the fluorescent intensity (F.I.) at 535 nm was detected using a plate reader (Perkin Elmer Japan Co., Ltd, ARVO Mx-3) (Ex: 485 nm). The degree of membrane fusion at each pH value was calculated using formula (1.1). Further, a degree of membrane fusion at each pH value relative to the degree of membrane fusion at pH 7.4 was calculated using formula (1.2). The measurement results of the degree of membrane fusion are shown in FIG. 4.

$$\text{Degree of membrane fusion} = \frac{I(x) - I(0)}{I(\infty) - I(0)} \quad \text{Formula (1.1)}$$

I (X)=Fluorescent intensity of anionic liposome and pH-responsive liposome
I (0)=Fluorescent intensity of only anionic liposome
I (∞)=Fluorescent intensity of anionic liposome treated with 0.5% SDS $$\text{Relative degree of membrane fusion} = \frac{D.F.(x)}{D.F.(7.4)} \quad \text{Formula (1.2)}$$

D.F. (X)=Degree of membrane fusion of anionic liposome and pH-responsive liposome at each pH value
D.F. (X)=Degree of membrane fusion of anionic liposome and pH-responsive liposome at pH 7.4

As understood from FIG. 4, the degree of membrane fusion remained almost unchanged in the pH range of 7.4 to 6.0, but increase in the degree of membrane fusion was recognized in the pH range of 6.0 to 4.0. Further, at pH 5.0, the degree of membrane fusion reached about 3.7 times the degree of membrane fusion at pH 7.4. This indicates that, in the pH-responsive liposome, the zeta potential changes from negative to positive under an environment of pH 5 to 6, and through electrostatic adsorption between the pH-responsive liposome and the anionic biomembrane, membrane fusion is promoted. The original data is as shown in Table 1.

TABLE 1

| | Fluorescent intensity at each pH value | | |
|---|---|---|---|
| pH | I(0)/— | I(x)/— | I(∞)/— |
| 7.4 | 1625 ± 133 | 2038 ± 265 | 2757 ± 68 |
| 7.0 | 1936 ± 175 | 2194 ± 107 | 2655 ± 119 |
| 6.5 | 1996 ± 91 | 2241 ± 345 | 2636 ± 45 |

TABLE 1-continued

| | Fluorescent intensity at each pH value | | |
|---|---|---|---|
| pH | I(0)/— | I(x)/— | I(∞)/— |
| 6.0 | 2059 ± 171 | 2301 ± 161 | 2614 ± 63 |
| 5.5 | 2098 ± 84 | 2618 ± 207 | 2601 ± 81 |
| 5.0 | 2131 ± 141 | 2789 ± 295 | 2623 ± 43 |
| 4.5 | 2232 ± 201 | 2587 ± 159 | 2533 ± 134 |
| 4.0 | 1646 ± 104 | 2121 ± 224 | 2726 ± 47 |

Example 3

Intracellular Kinetics of pH-Responsive Liposome (Preparation of TRITC-Labeled Albumin-Encapsulated Liposome)

2 mg of tetramethylrhodamine-5-(and-6)-isothiocyanate (TRITC) was dissolved in 0.1 N—NaOH aq. to adjust pH to 7.4. The aqueous solution was mixed with 1 mL of albumin (25 g/dL) and stirred for 3 hours. After that, unlinked rhodamine was removed using a gel column (Sephadex G-25) to prepare rhodamine-labeled albumin.

Next, 25 μl of pH-responsive mixed lipid (Compound 3/cholesterol/PEG-Glu2C$_{18}$=5/5/0.03, molar ratio) was hydrated with an aqueous solution of the rhodamine-labeled albumin (10 mg/mL), and albumin-encapsulated liposome (hereinafter sometimes referred to as rhodamine-labeled albumin-encapsulated pH-responsive liposome) was prepared using the high-pressure extrusion method (final pore diameter: 0.22 μm).

<Analysis of Intracellular Kinetics of Albumin-Encapsulated Liposome Using Confocal Microscope>

In order to analyze release behavior of the substance encapsulated by liposome after taken into a cell, observation of intracellular kinetics was carried out using a confocal microscope. Firstly, 1×10$^5$ COS-7 cells (kidney cells from African green monkey) were seeded in a 35 mm glass-bottomed dish and cultured for 24 hours (37° C., 5% CO$_2$). Subsequently, each liposome, which was diluted with Dulbecco's Modified Eagle Medium (DMEM) (10% bovine serum), was added to the cells ([lipid]=50 μg/dish) and cultured for 2 hours. Subsequently, after washed with PBS(−) twice, an endosome or lysosome was stained using Lysotracker (450 nM). Then, localization of the encapsulated rhodamine-labeled albumin (red) and the endosome (green) was observed using a confocal microscope (LSM5 Pascal, Carl Zeiss Co., Ltd.). In addition, CCD-32SK cells were also substituted in a MEM medium, and kinetics of liposomes taken into the cells was observed in the same way. The results are shown in FIG. 5.

Figure 5:
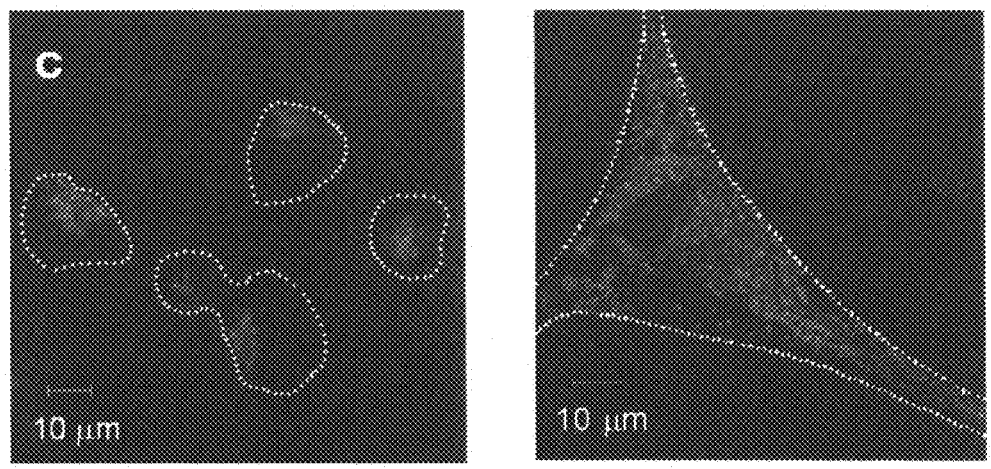
FIG. 5 is a confocal microscope photograph showing intracellular kinetics of a rhodamine-labeled albumin-encapsulated liposome comprising (Compound 3)/cholesterol/PEG-Glu2C$_{18}$ as a membrane component in COS-7 and CCD-32SK.

As understood from FIG. 5, with respect to rhodamine-labeled albumin-encapsulated pH-responsive liposome, a portion in which albumin was solely localized was observed, and it was suggested that albumin had been released from the endosome. This indicates that the pH-responsive liposome can deliver albumin contained in the liposome into cytoplasm.

Example 4

Preparation of siRNA-Encapsulated Liposome

Compound 3 obtained in Example 1 (20 mg) was hydrated with 500 μL of 10 nmol/mL siRNA (21 bp) aqueous solution dispersed in an aqueous solution of 0.1% DEPC (diethyl pyrocarbonate) for 6 hours, and then a siRNA-encapsulated liposome was prepared using the high-pressure extrusion method (final pore diameter: 0.22 μm). Further, a liposome in which siRNA is not encapsulated was prepared in a manner similar to that described above except that no siRNA was added.

<Evaluation of Luciferase Synthesis Inhibition by siRNA-Encapsulated pH-Responsive Liposome>

Figure 6:
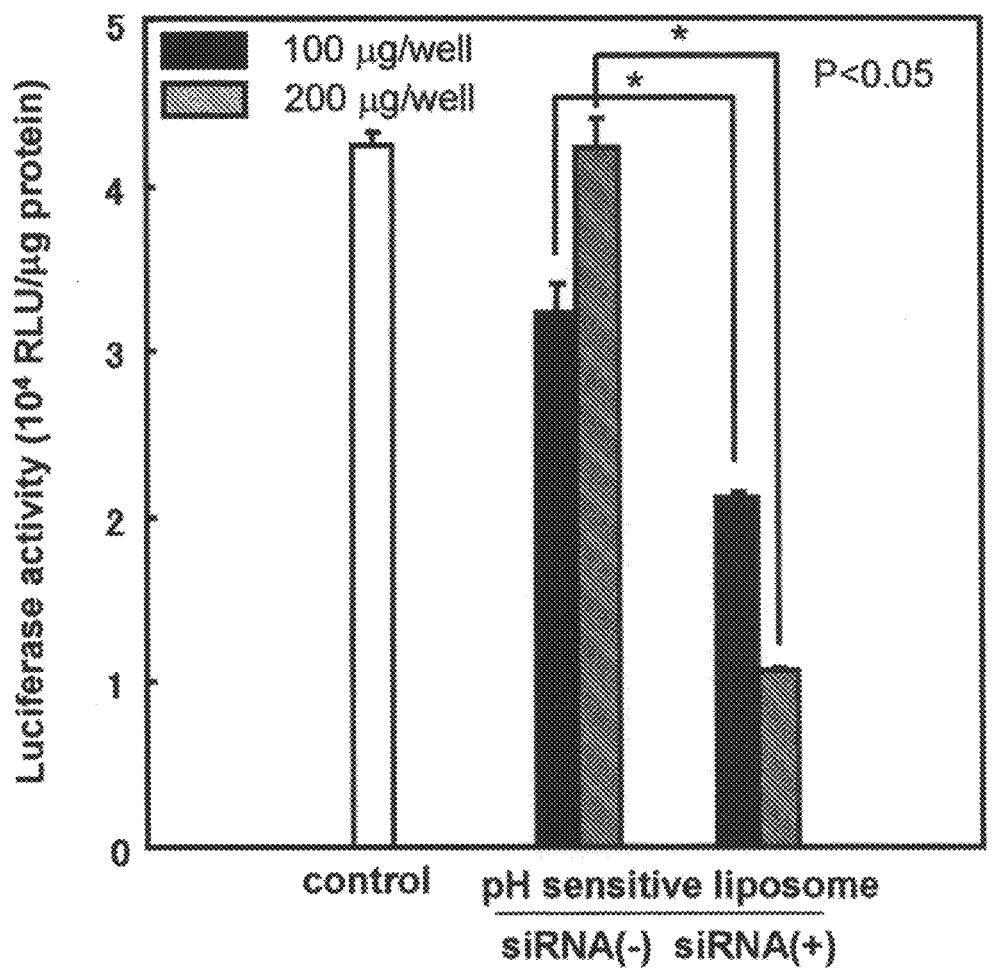
FIG. 6 is a graph showing evaluation results regarding suppression of gene expression in luciferase protein expressing CHO cells caused by a siRNA-encapsulated liposome comprising (Compound 3)/cholesterol/PEG-Glu2C$_{18}$ as a membrane component.

A CHO cell in which the luciferase protein synthesis gene is constantly expressed was prepared, and synthesis inhibition by RNAi after addition of the siRNA-encapsulated liposome was evaluated. $5 \times 10^4$ luciferase expressing CHO cells were seeded in a 12-well plate and cultured for 24 hours (37° C., 5% $CO_2$). After that, the siRNA-encapsulated liposome was added to the cells in the presence of serum ([lipid]=100 or 200 μg/well) and cultured for 24 hours (37° C., 5% $CO_2$). After washed with PBS(−) twice, the cells were solubilized. Then the luminescence intensity after substrate addition was measured, and the expression level of luciferase was calculated. The results are shown in FIG. 6. As a control, only medium was added. In FIG. 6, the siRNA-encapsulated liposome is represented by siRNA(+), and the liposome in which siRNA is not encapsulated is represented by siRNA(−).

As understood from FIG. 6, as the additive amount increased, the expression level of luciferase significantly decreased, and in the case of [Lipid]=100 μg/well, about 50% inhibition of luciferase synthesis was accomplished, and in the case of [Lipid]=200 μg/well, about 75% inhibition of luciferase synthesis was accomplished. This means: the pH-responsive liposome allowed siRNA to escape from endosome to cytoplasm; inhibition of luciferase synthesis was caused by siRNA; and it contributed to knockdown of the amount of luciferase expressed in the cells. This result indicates that the molecular assembly of the present invention is a useful carrier for gene therapy utilizing RNAi.

<Toxicity Assessment of pH-Responsive Liposome>

The toxicity assessment of the pH-responsive liposome was carried out using WST Assay. $1 \times 10^4$ luciferase expressing CHO cells were seeded in a 96-well plate and cultured for 24 hours (37° C., 5% $CO_2$). After that, the liposome was added to the cells in the presence of serum ([lipid]=5, 10, 20 or 40 μg/well) and cultured for 24 hours (37° C., 5% $CO_2$). Subsequently, after washed with DMEM (10% FBS) twice, WST1/ECS reagent (ImmunoKontact) was added thereto. After cultured for 1 hour (37° C., 5% $CO_2$), the absorbance at 450 nm was measured using a plate reader. The cell survival rate was calculated using the following formula. The results are shown in FIG. 7.

$$\text{Cell survival \%} = \frac{I_x - I_0}{I_{100} - I_0}$$

Figure 7:
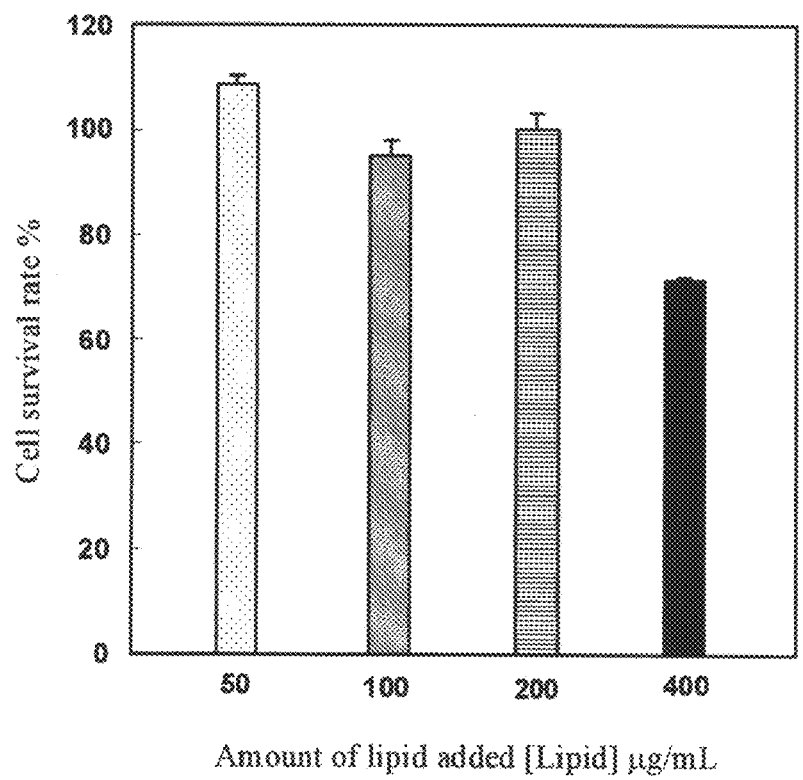
FIG. 7 is a graph showing evaluation results regarding cytotoxicity of a liposome comprising (Compound 3)/cholesterol/PEG-Glu2C$_{18}$ as a membrane component.

$I_0$: without cells, $I_{100}$: without addition of liposome, $I_x$: liposome was added As understood from FIG. 7, in the case of the pH-responsive liposome, when the amount of lipid added ([Lipid] μg/mL) was 20 μg/well or smaller, the cell survival rate was nearly 100%, and when the amount added was 40 μg/well, the cell survival rate was nearly 70%. The cell test was carried out using the 96-well plate, but the measurement of luciferase activity was carried out using the 12-well plate. Therefore, the result of the toxicity assessment is converted into a value in the case of the 12-well plate. Then, it can be analogized that no cytotoxicity was exerted in the case of addition of 200 μg/well. Therefore, it can be said that decrease in luciferase expression in the cytoplasm was caused not by the toxicity from the liposome membrane lipid, but by siRNA delivered from the pH-responsive liposome.

Example 5

Test of In Vivo Distribution of Bovine Serum Albumin (BSA)-Encapsulated pH-Responsive Liposome Regarding a BSA-encapsulated pH-responsive liposome, the concentration of Compound 3 in rat plasma and tissue was measured. Regarding the BSA-encapsulated pH-responsive liposome, the concentration of Compound 3 in rat plasma and tissue was measured using LC/MS/MS.

For analysis of the disposition of the pH-responsive liposome, the following analysis equipments were utilized.
Centrifuge: MX-301 (Tomy Seiko Co., Ltd.)
HPLC: LC-20A System (Shimadzu Corporation)
　System controller: SCL10Avp
　Pump: LC-20AD
　Degasser: DGU-20A3
　Autoinjector: SIL-20AC
　Column oven: CTO-20AC
MS: API2000 (Applied Biosystems/MDS SCIEX)
　Interface: Turbo Ion Spray <Experiment of Administration>

A pH-responsive liposome was prepared from mixed lipid (Compound (3)/cholesterol/PEG-Glu2C$_{18}$=5/5/0.03 (mol)) using the high-pressure extrusion method. In the preparation, the particle size of the liposome was adjusted to 200 to 250 nm. Further, BSA was encapsulated in the internal aqueous phase. The prepared pH-responsive liposome ([Lipid]=20 mg/mL) was intravenously administered to a SD rat (male, body weight of 300 g or less) via the tail vein in an amount of 2 ml/kg under ether anesthesia. The number of rats used was N=3. Prior to the administration and 5 minutes, 1, 2, 6 and 24 hours after the administration, blood was collected (about 500 μL). The obtained blood was subjected to centrifugation (2,000×g, 20 minutes) to obtain plasma (liposome-suspended plasma), and this was preserved at −80° C. Further, after blood was collected 24 hours after the administration, the liver, spleen, lung and kidney were isolated, the wet weight thereof was measured, and these materials were preserved at −80° C. After that, homogenization was carried out using a saline in an amount 4 times greater than the wet weight of the organs.

<Method for Preparation of Samples for Measurement>

—Sample for Analysis of Calibration Curve and LC-MS

A material in which the procedure is carried out until 100 μL of GGLG standard solution is added to 10 μL of plasma and liver homogenate solution was used as a sample for measurement of calibration curve.

—Sample for Measurement of Specimen

A material in which the procedure is carried out until 100 μL of methanol is added to 10 μL of homogenate solution of plasma and the organs was used as a sample for measurement of specimen.

To the above-described sample for measurement, a solution to which an internal standard material (1,5-dihexadecyl N-glutamyl-L-glutamate (αGlu-Glu2C$_{16}$)) was added (900 μL) was added, and the mixture was subjected to vortex stirring. After that, the mixture was allowed to stand at room temperature for at least 10 minutes. After that, the mixture was subjected to vortex stirring again and centrifuged at 4° C. at 10,000×g for 15 minutes. The obtained supernatant was transferred to an LC vial.

High-Performance Liquid Chromatography (HPLC)—Tandem Mass Spectrometry (MS/MS) (LC/MS/MS)

Conditions for HPLC

As a column, CAPLCELLPAK $C_{18}$ MG (Shiseido Co., Ltd.) (3 µm, 2.0×50 mm) was used, and the column temperature was set at 40° C. Gradient elution was carried out using 0.1% acetic acid aqueous solution (A)-0.1% methanol acetate (B). The flow rate was 0.25 mL/min. The gradient program is as shown in Table 2. The temperature of the autoinjector was set at 15° C. Regarding a needle washing solution, chloroform/methanol (1:1) was used for a washing pump, and methanol was used for a washing port.

TABLE 2

| Time (minutes) | B content (%) |
|---|---|
| 0 | 85 |
| 5 | 100 |
| 10 | 100 |
| 10.1 | 85 |
| 15 | 85 |

Conditions for MS/MS

The eluent that was separated by HPLC was subjected to positive ESI ionization and measured in the MRM mode. The parameters are as shown in Table 3.

TABLE 3

| | Compound 3 (GGLG) | Internal standard material (αGlu-Glu2C$_{16}$) |
|---|---|---|
| DP | 151.00 | 146.00 |
| FP | 360.00 | 290.00 |
| EP | 10.50 | 6.00 |
| CE | 129.00 | 95.00 |
| CXP | 0.00 | 0.00 |
| CUR | | 30.0 |
| CAD | | 3 |
| IS | | 5000.0 |
| TEM | | 400.0 |
| GS1 | | 25.0 |
| GS2 | | 60.0 |
| Ihe | | ON |
| Detection | 982.92→84.20 m/z | 725.71→84.20 m/z |

As an internal standard material, αGlu-Glu2C$_{16}$, which has a structure similar to that of Compound 3, and which is represented by the formula below, was used.

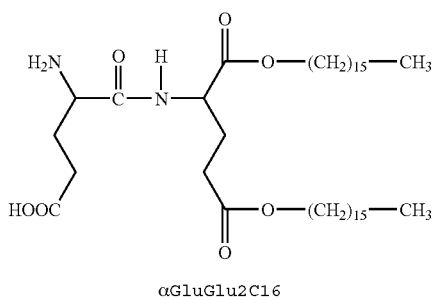

αGluGlu2C16

Concentration of Compound 3 (GGLG) in Plasma and Pharmaceutical Preparation

Figure 8:
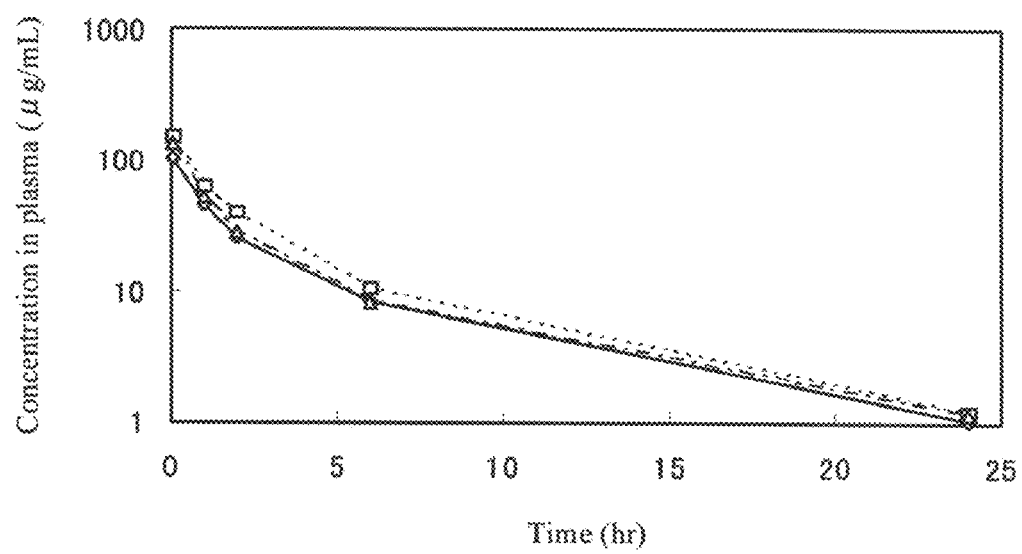
FIG. 8 is a graph showing measurement results of time-dependent change in the concentration of Compound 3 in plasma after administration of a liposome comprising (Compound 3)/cholesterol/PEG-Glu2C$_{18}$ as a membrane component, which was measured using LC/MS/MS.

An analyte for producing a calibration curve for measurement of plasma was measured, and a calibration curve of 1-300 µg/mL of plasma was prepared with weighting of $1/x^2$ and Quadratic. The peak area of the analyte for measurement of plasma/IS peak area was substituted into the obtained formula of the calibration curve to calculate the concentration of Compound 3 in plasma. The results are shown in Table 4. FIG. 8 is a graph showing the results. In FIG. 8, (-◇-), (--□--) and (--Δ--) show the results of animal 1, animal 2 and animal 3, respectively. PK parameters are as shown in Table 5.

TABLE 4

Concentration of Compound 3 (GGLG) in plasma

| | GGLG concentration in plasma (µg/mL) | | | | |
|---|---|---|---|---|---|
| | animal 1 | animal 2 | animal 3 | Average value | Standard deviation |
| Pre | N.D. | N.D. | N.D. | — | |
| 5 min | 105.30 | 153.13 | 136.28 | 131.57 | 24.25 |
| 1 hr | 44.72 | 62.44 | 53.49 | 53.55 | 8.86 |
| 2 hr | 25.81 | 39.28 | 28.50 | 31.20 | 7.13 |
| 6 hr | 8.39 | 10.20 | 8.12 | 8.90 | 1.13 |
| 24 hr | 1.02 | 1.20 | 1.17 | 1.13 | 0.0940 |

N.D.: less than lower limit of quantitation

TABLE 5

PK parameters

| | animal 1 | animal 2 | animal 3 | Average |
|---|---|---|---|---|
| Tmax (hr) | 0.083 | 0.083 | 0.083 | 0.083 |
| Cmax (ug/mL) | 105.31 | 153.13 | 136.30 | 131.57 |
| AUC(hr*ug/mL) | 266.21 | 364.43 | 296.59 | 309.08 |
| t½(hr) | 5.032 | 4.31 | 5.18 | 4.84 |

It was understood from the concentration of Compound 3 in plasma in the LC/MS/MS measurement that the half-life of Compound 3 is 4.8 hours. According to the above-described results, it was understood that the pH-responsive liposome containing Compound 3 exhibits good retention property in the blood.

<Concentration of Compound 3 (GGLG) in Tissue>

Figure 9:
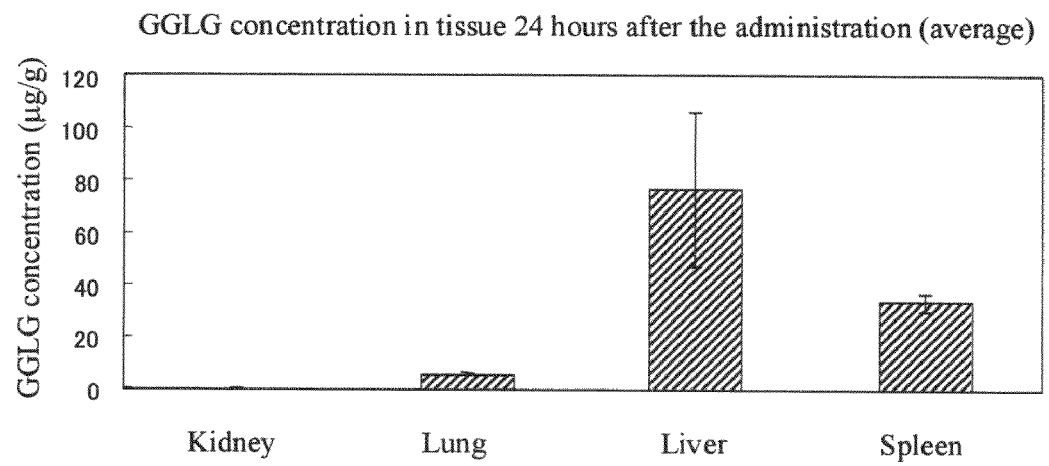
FIG. 9 is a graph showing measurement results of distribution of Compound 3 in the organs after administration of a liposome comprising (Compound 3)/cholesterol/PEG-Glu2C$_{18}$ as a membrane component, which was measured using LC/MS/MS.

An analyte for producing a calibration curve for measurement of tissue was measured, and a calibration curve of 1-100 µg/ml was prepared with weighting of $1/x^2$ and Quadratic. The peak area of the analyte for measurement of tissue/IS peak area was substituted into the obtained formula of the calibration curve to calculate the concentration of Compound 3 in tissue (in the calculation, the specific gravity of the tissue homogenate was regarded as 1 g/mL). The results are shown in Table 6. FIG. 9 is a graph showing the results.

TABLE 6

Concentration of Compound 3 in tissue (µg/g)

| | animal 1 | animal 2 | animal 3 | Average value | Standard deviation |
|---|---|---|---|---|---|
| Kidney | N.D. | N.D. | N.D. | — | — |
| Lung | 5.60 | 5.02 | 6.17 | 5.60 | 0.58 |
| Liver | 110.32 | 64.38 | 55.62 | 76.78 | 29.38 |
| Spleen | 30.35 | 33.45 | 36.7 | 33.53 | 3.22 |

N.D.: less than lower limit of quantitation

With respect to the distribution of Compound 3 in the organs 24 hours after the administration in the LC/MS/MS measurement, Compound 3 was mainly localized in the liver and spleen. This was the same as the case of the distribution of a usual liposomal preparation in the organs. Almost no Compound 3 was localized in the kidney and lung. This indicates that the pH-responsive liposome has retention property in the blood. Accordingly, it is understood that the pH-responsive liposome is useful as a carrier for a drug, probe, nucleic acid and protein which targets organs.

Example 6

Synthesis of pH-Responsive Amphiphilic Molecule

Compound 1 obtained in Step (A) in Example 1 (1.0 g, 1.67 mmol) and triethylamine (202 mg, 2.0 mmol) were dissolved in 30 mL of dichloromethane and stirred at room temperature for 1 hour. Then, lysine (617 mg, 1.4 mmol), in which a γ amino group and a ε amino group were protected by a t-butoxycarbonyl (Boc) group and a benzyloxycarbonyl (Z) group, respectively, and a carboxyl group was activated by N-hydroxysuccinimide, was added thereto, and stirred at room temperature for another 6 hours. After the reaction completed, the solvent was removed under reduced pressure. The resultant solution was dissolved in chloroform, and washed with a saturated aqueous solution of sodium carbonate 3 times. The chloroform layer was dehydrated with magnesium sulfate. The resultant substance was filtered, and then the solvent was removed under reduced pressure. The residue was recrystallized with methanol at 4° C. and filtered with a glass filter (G6). After freeze-dried, Compound 4 was obtained.

Compound 4

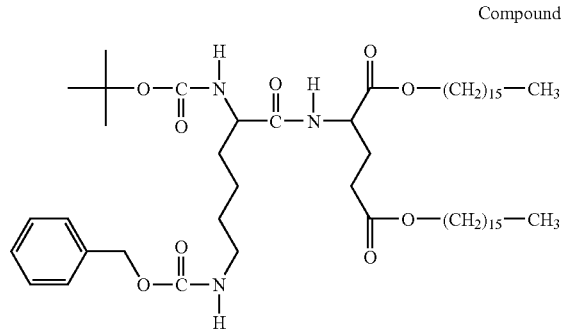

Compound 4 was subjected to the TFA treatment to deprotect a Boc group, dissolved in chloroform, and washed with a saturated aqueous solution of sodium carbonate 3 times. After washed with pure water, the chloroform layer was dehydrated with magnesium sulfate. The resultant substance was filtered, and then the solvent was removed under reduced pressure to obtain Compound 5.

Compound 5

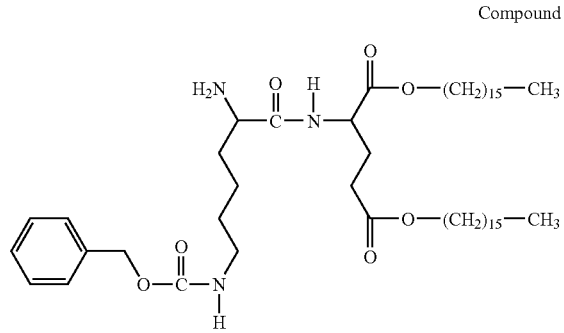

Compound 5 (500 mg, 0.58 mmol) and triethylamine (71 mg, 0.70 mmol) were dissolved in 30 mL of dichloromethane and stirred at room temperature for 1 hour. Then, glutamic acid Boc-Glu(OtBu)-OSu (310 mg, 0.7 mmol), in which an α amino group and a γ-carboxyl group were protected by a Boc group and a OtBu group, respectively, and an α-carboxyl group was activated by N-hydroxysuccinimide, was added thereto, and stirred at room temperature for another 6 hours to cause a reaction. After the reaction completed, the solvent was removed under reduced pressure. The resultant solution was dissolved in chloroform, and washed with a saturated aqueous solution of sodium carbonate 3 times. The chloroform layer was dehydrated with magnesium sulfate. The resultant substance was filtered, and then the solvent was removed under reduced pressure. The residue was recrystallized with methanol at 4° C. and filtered with a glass filter (G6). After freeze-dried, Compound 6 was obtained.

Compound 6

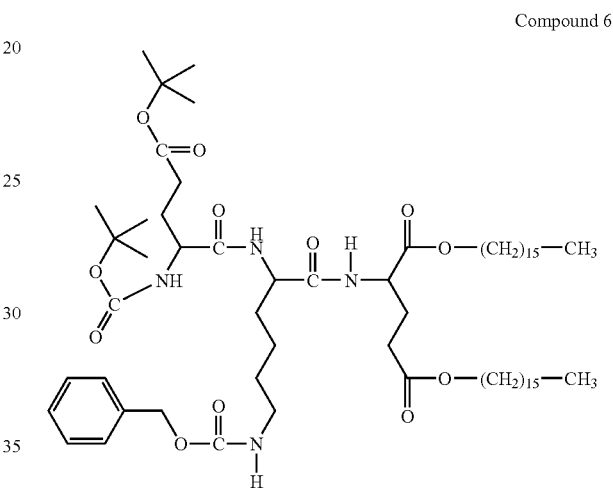

In the presence of H$_2$/Pd-Black, Compound 6 was reacted with aspartic acid Boc-Asp(OtBu)-OSu, in which: a Z group was deprotected; a α amino group and a β carboxyl group were protected by a Boc group and a OtBu group, respectively; and an a carboxyl group was activated by N-hydroxysuccinimide. Deprotection was performed with TFA, and Compound 7 (Ia-2) was obtained.

Compound 7

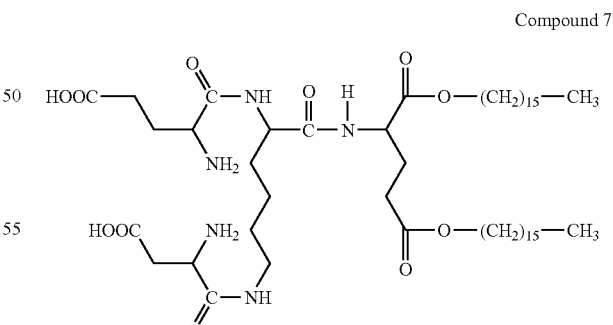

Identification of Compound 7 (Ia-2):
Thin layer chromatography (silica gel, chloroform/methanol (5/1) (volume/volume): R$_f$: 0.05 (monospot))
$^1$H-NMR (CDCl$_3$, 500 MHz, δ (ppm)): 0.88 (t, 6H, —CH$_3$); 1.30 (br, 52H, alkyl); 1.62 (m, 4H, COO—CH$_2$—CH$_2$—); 4.28 (q, 1H, lys α-CH—); 4.47 (q, 1H, glu α-CH—COO—);

Compound 8 (Ia-4) was synthesized in a manner similar to that for obtaining Compound 7, except that Boc-Asp(OtBu)-OSu and Boc-Glu(OtBu) were used instead of Boc-Glu(OtBu) and Boc-Asp(OtBu)-OSu, respectively.

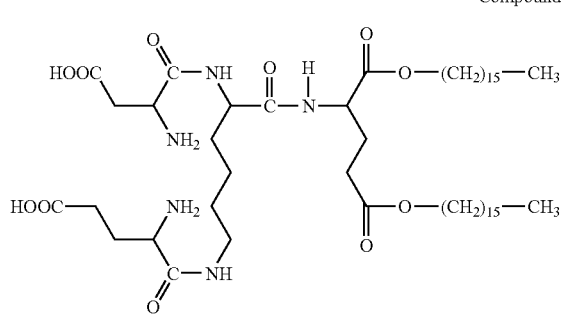

Compound 8

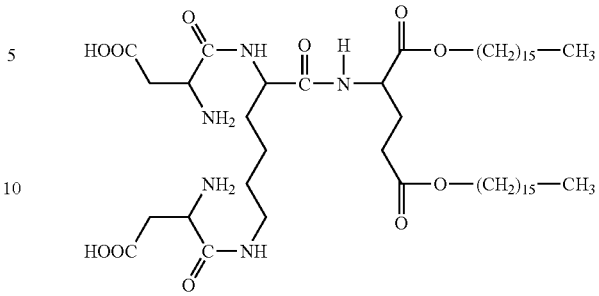

Compound 9

Identification of Compound 9 (Ia-3):

Thin layer chromatography (silica gel, chloroform/methanol (5/1) (volume/volume): $R_f$: 0.15 (monospot))

$^1$H-NMR (CDCl$_3$, 500 MHz, δ (ppm)): 0.83 (t, 6H, —CH$_3$); 1.24 (br, 52H, alkyl); 3.64, 3.88 (t, 1H, Asp α-CH-Lys-); 4.33 (q, 1H, lys α-CH—); 4.61 (q, 1H, Asp α-CH—COO—)

Example 7

Preparation of Liposome

Identification of Compound 8 (Ia-4):

Thin layer chromatography (silica gel, chloroform/methanol (5/1) (volume/volume): $R_f$: 0.07 (monospot))

$^1$H-NMR (CDCl$_3$, 500 MHz, δ (ppm)): 0.84 (t, 6H, —CH$_3$); 1.23 (br, 52H, alkyl); 3.68, 3.94 (t, 1H, glu α-CH-Lys-); 4.34 (q, 1H, lys α-CH—); 4.60 (q, 1H, glu α-CH—COO—)

Compound 2 obtained in Step (B) in Example 1 (500 mg, 691 mmol) and triethylamine (107 μl, 829 mmol) were dissolved in 30 mL of dichloromethane and stirred at room temperature for 1 hour. Then, aspartic acid Boc-Asp(OtBu)-OSu (639 mg, 1.45 mmol), in which an amino group and a β carboxyl group were protected by a Boc group and a t-butyl-ester group, respectively, and an α-carboxyl group was activated by N-hydroxysuccinimide, was added thereto, and stirred at room temperature for another 6 hours to cause a reaction.

After the reaction completed, the solvent was removed under reduced pressure. The resultant solution was dissolved in chloroform, and washed with a saturated aqueous solution of sodium carbonate 3 times. The chloroform layer was dehydrated with magnesium sulfate. The resultant substance was filtered, and then the solvent was removed under reduced pressure. The residue was recrystallized with methanol at 4° C. and filtered with a glass filter (G6) to obtain a lysine derivative having a protected amino group.

To the obtained lysine derivative, trifluoroacetic acid (20 mL) was added and stirred at 4° C. for 2 hours. After the reaction completed, the solvent was removed under reduced pressure. The resultant solution was dissolved in chloroform, and washed with a saturated aqueous solution of sodium carbonate twice. The chloroform layer was dehydrated with magnesium sulfate. The resultant substance was filtered, and then the solvent was dried under reduced pressure to obtain Compound 9 (Ia-3), the amphiphilic molecule of the present invention, as white powder.

Compound 7, 8 or 9 (0.177 mmol), cholesterol (0.179 mmol) and PEG-Glu2C$_{18}$ (1.0 μmol) were dissolved in benzene, and the mixture was freeze-dried to prepare a mixed lipid. 20 mg of this mixed lipid was dispersed in 1 mL of water for injection, and the resultant mixture was stirred for 6 hours. After that, liposome having a particle size of about 240 nm was prepared by means of the high-pressure extrusion method (final pore diameter: 0.22 μm).

Portions of the prepared liposome ([lipid]=10 mg/ml) were respectively added to acetate buffers with different pHs (7.4, 7, 6, 5, 4) (20 mM) to the final concentration of [lipid]=1 mg/mL, and then the zeta potential at 37° C. was measured.

It is thought that, in the case where Compound 9 (Ia-3) was used as the main component, it was aggregated when the mixed lipid having this lipid composition was dispersed in water and filtered at the time of high-pressure extrusion. It is considered that a lipid in which aspartic acid is used for the hydrophilic moiety is probably less likely to be hydrated.

Figure 10:
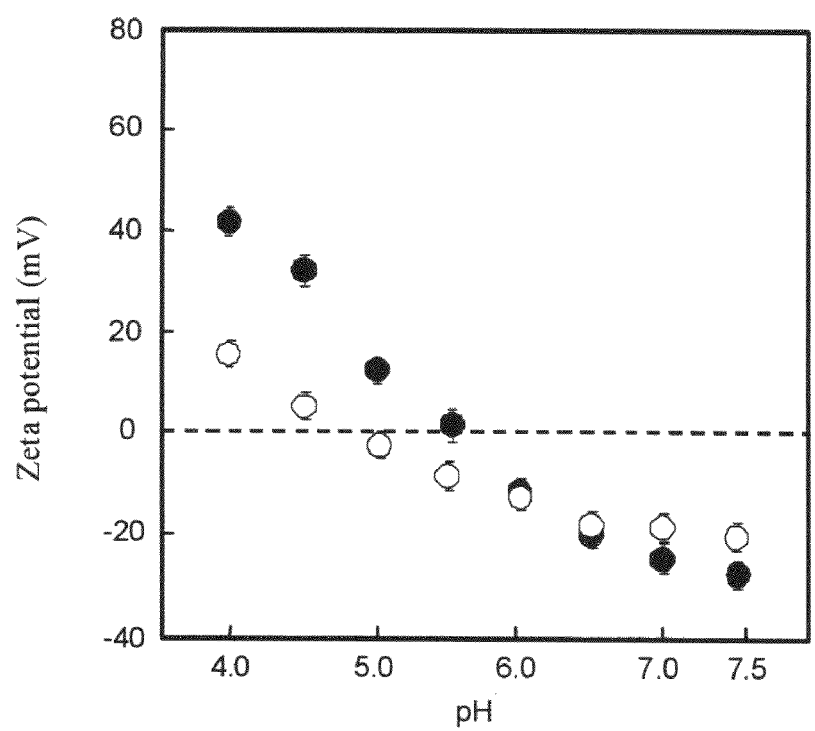
FIG. 10 is a graph showing measurement results of the zeta potential of liposomes comprising (●) Compound 7/cholesterol/PEG-Glu2C18 (5/5/0.03 (molar ratio)) or (○) Compound 8/cholesterol/PEG-Glu2C18 (5/5/0.03 (molar ratio)) as a membrane component.

On the other hand, in the case where Compound 7 was used as the main component, and in the case where Compound 8 was used as the main component, liposome was formed. In FIG. 10, (●) shows change in the zeta potential of the liposome comprising Compound 7 as the main component (Compound 7/cholesterol/PEG-Glu2C18 (5/5/0.03 (molar ratio))), and (○) shows change in the zeta potential of the liposome comprising Compound 8 as the main component (Compound 8/cholesterol/PEG-Glu2C18 (5/5/0.03 (molar ratio))). In the case of the liposome comprising Compound 7 (Ia-2) as the main component, the pH at which the zeta potential changed from negative to positive was about 5.5. In the case of the liposome comprising Compound 8 (Ia-4) as the main component, the pH as described above was about 4.8. According to the results, it became clear that an amphiphilic molecule in which glutamic acid or aspartic acid is used for the hydrophilic moiety forms a liposome and exhibits pH-responsiveness in which the zeta potential changes depending on pH change.

Example 8

Synthesis of Zwitterionic Lipids with Different Alkyl Chain Length

In a manner similar to that in Step (A) in Example 1, Compound 10 (1,5-tetradecyl-L-glutamate) and Compound 11 (1,5-octadecyl-L-glutamate), whose alkyl chain lengths are 14 and 18, respectively, were synthesized using glutamic acid and tetradecyl alcohol or stearyl alcohol.

Compound 10

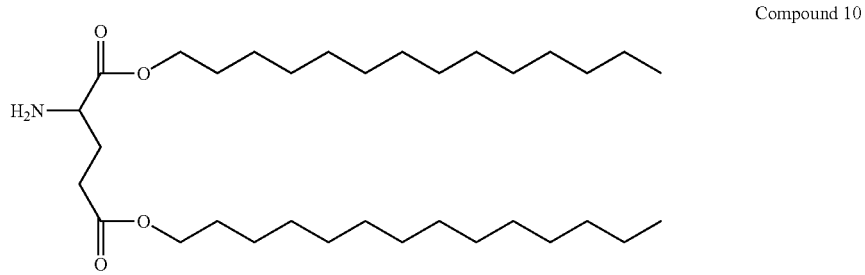

Compound 11

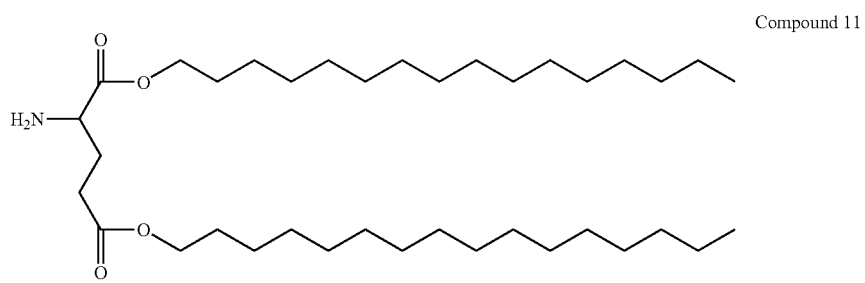

Compound 12 and Compound 13, each of which has 2 glutamic acids in the hydrophilic moiety, wherein the alkyl chain of Compound 12 is different from that of Compound 13, were synthesized using Compound 10 and Compound 11, respectively.

Compound 12

-continued

Compound 13

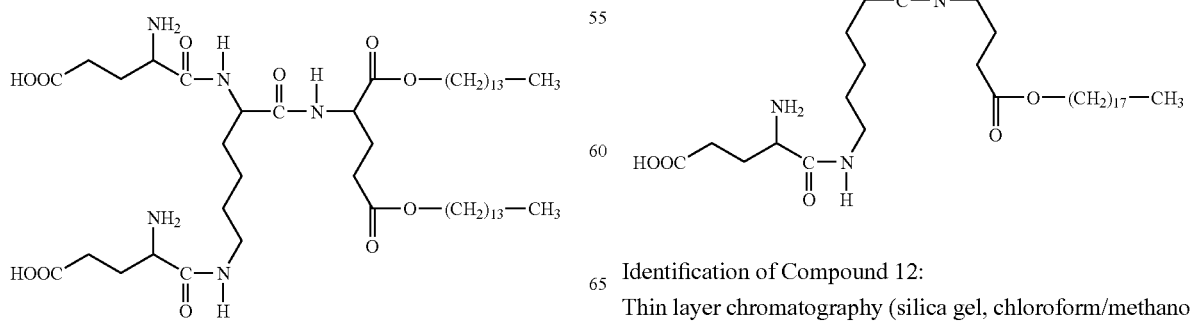

Identification of Compound 12:

Thin layer chromatography (silica gel, chloroform/methanol (5/1) (volume/volume): $R_f$: 0.05 (monospot))

$^1$H-NMR (CDCl$_3$, 500 MHz, δ (ppm)): 0.88 (t, 6H, —CH$_3$); 1.27 (br, 44H, alkyl); 1.55 (br, 4H, COO—CH$_2$—CH$_2$—), 4.34 (q, 1H, lys α-CH—); 4.44 (q, 1H, glu α-CH—COO—)

Identification of Compound 13:

Thin layer chromatography (silica gel, chloroform/methanol (5/1) (volume/volume): R$_f$; 0.04 (monospot))

$^1$H-NMR (CDCl$_3$, 500 MHz, δ (ppm)): 0.88 (t, 6H, —CH$_3$); 1.27 (br, 60H, alkyl); 1.65 (br, 4H, COO—CH$_2$—CH$_2$—), 4.12 (t, 1H, glu α-CH-Lys-); 4.35 (q, 1H, glu α-CH—COO—); 3.60 (t, 4H, COO—CH$_2$—CH$_2$—)

Example 9

Preparation of Liposomes and Measurement of Zeta Potential and Degree of Fusion

Liposomes which include Compounds 3, 12 and 13, respectively, as its constituent were prepared. The zeta potential and the degree of fusion of each of the obtained liposomes were measured, and the physical properties were compared to each other.

<Preparation of Liposome>

Compound 3, 12 or 13 (0.177 mmol), cholesterol (0.179 mmol) and PEG-Glu2C$_{18}$ (1.0 mmol) were dissolved in benzene, and the mixture was freeze-dried to prepare a mixed lipid. 20 mg of this mixed lipid was dispersed in 1 mL of water for injection, and the resultant mixture was stirred for 6 hours. After that, liposome having a particle size of about 240 nm was prepared by means of the high-pressure extrusion method (final pore diameter: 0.22 μm).

<Measurement of Zeta Potential>

Figure 11:
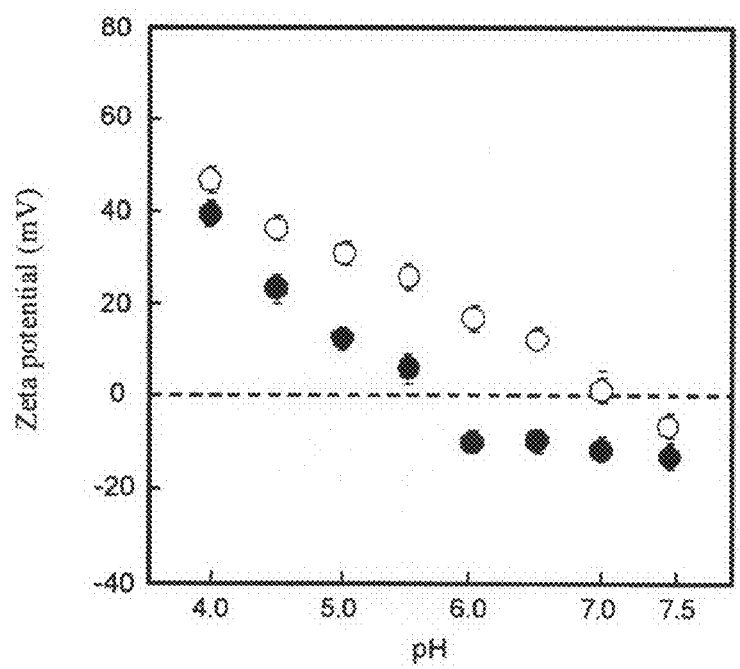
FIG. 11 is a graph showing measurement results of the zeta potential of liposomes comprising (●) Compound 3/cholesterol/PEG-Glu2C18 (5/5/0.03 (molar ratio)) or (○) Compound 12/cholesterol/PEG-Glu2C18 (5/5/0.03 (molar ratio)) as a membrane component.

Portions of each of the prepared liposomes ([lipid]=10 mg/ml) were respectively added to acetate buffers with different pHs (7.4, 7, 6, 5, 4) (20 mM) to the final concentration of [lipid]=1 mg/mL, and then the zeta potential at 37° C. was measured. The results are shown in FIG. 11. In FIG. 11, (●) shows change in the zeta potential of the liposome comprising Compound 3 as the main component (Compound 3/cholesterol/PEG-Glu2C18 (5/5/0.03 (molar ratio))), and (○) shows change in the zeta potential of the liposome comprising Compound 12 as the main component (Compound 7/cholesterol/PEG-Glu2C18 (5/5/0.03 (molar ratio))).

In the case where Compound 13 was used as the main component, the prepared mixed lipid showed poor dispersibility at the time of being dispersed in water, aggregated, and filtered at the time of high-pressure extrusion. It is thought that this is because Compound 13, which has a large hydrophobic moiety, has inappropriate hydrophobic-hydrophilic balance in this lipid composition and does not easily form a vesicular structure. On the other hand, in the case where Compound 3 was used as the main component, and in the case where Compound 12 was used as the main component, liposome was formed. In the case of the liposome comprising Compound 3 as the main component, the pH at which the zeta potential changed from negative to positive was about 5.7. In the case of the liposome comprising Compound 12 as the main component, the pH as described above was about 7.0. According to the results, it became clear that the zeta potential behavior varies depending on the alkyl chain length of the hydrophobic moiety even when the structure of the hydrophilic moiety in the amphiphilic molecule as the liposome membrane component is the same.

<Measurement of the Degree of Fusion>

Figure 12:
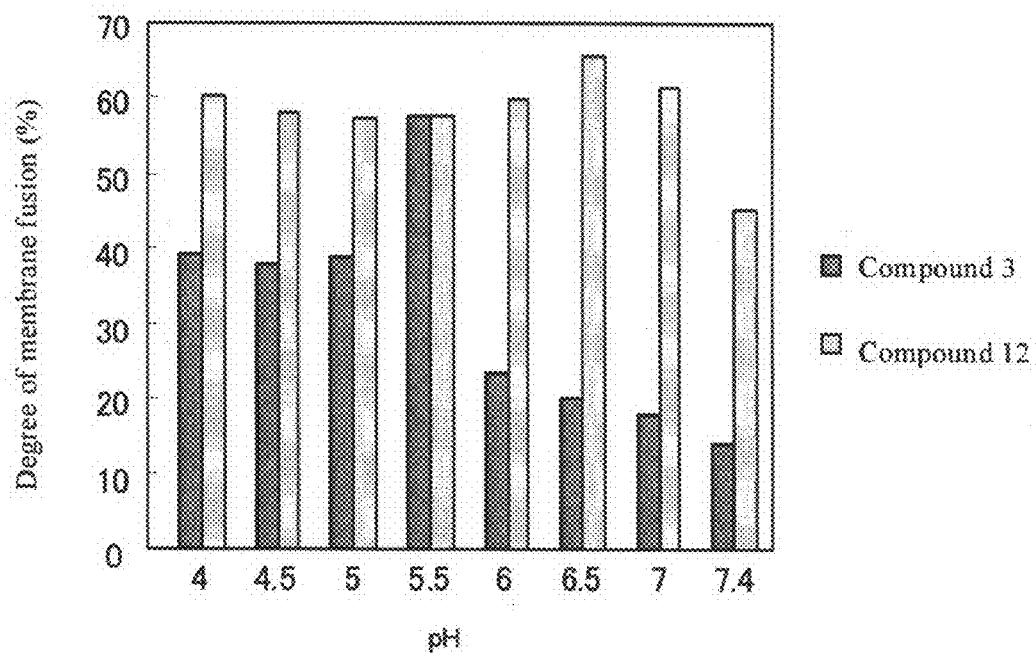
FIG. 12 is a graph showing the relative degree of membrane fusion of a liposome comprising Compound 3 or 12 as a membrane component and an anionic liposome at each pH.

In a manner similar to that in Example 2, the degree of fusion of the pH-responsive liposome with respect to the anionic liposome (DOPC/DPPG, 5/1 (molar ratio)) was calculated. The measurement method was as follows. 50 μL of 1 mM anionic liposome and 50 μL of 9 mM (converted to the mixed lipid basis) pH-responsive liposome were added to 1.9 mL of each of acetate buffers with different pHs and allowed to stand at 37° C. 30 minutes later, 100 mL of the mixture was dividedly poured and added to 1.9 mL of HEPES buffer (pH 7.4). The resultant mixture was transferred to a quartz cell and subjected to fluorescence measurement ($\lambda_{ex}$: 460 nm, 530 nm). The measurement was carried out using RF-5300PC manufactured by Shimadzu. The results are shown in FIG. 12.

In the case of the liposome comprising Compound 3 as the main component, the degree of fusion at pH 7.4 was about 15% as previously reported, but at pH 5.5, the degree of fusion was maximum and the value thereof was about 60%. On the other hand, in the case of the liposome comprising Compound 12, whose alkyl chain length is 14, as the main component, the degree of fusion was high (about 45%) even at pH 7.4, and the degree of fusion was maximum at pH 6.5, wherein the value thereof was over 65%.

In view of the results of the measurement of the zeta potential, since the zeta potential of Compound 12 became positive even in the neutral region and the phase transition temperature thereof was low, it is speculated that Compound 12 can be easily fused with the anionic liposome.

Example 10

Evaluation of Luciferase Synthesis Inhibition by siRNA-Encapsulated Liposome

<Preparation of siRNA-Encapsulated Liposome>

A group of siRNA-encapsulated or siRNA-nonencapsulated liposomes consisting of dipalmitoylphosphatidylcholine (DPPC)/cholesterol/DHSG/PEG-Glu2C18 (5/5/1/0.033, molar ratio), which is a conventionally-used lipid composition (liposome 1), and a group of siRNA-encapsulated or siRNA-nonencapsulated liposomes consisting of αGluGlu2C16/cholesterol/PEG-Glu2C18 (5/5/0.03, molar ratio) (liposome 2) were prepared, and these groups were compared to a group of siRNA-encapsulated or siRNA-nonencapsulated liposomes consisting of Compound 3/cholesterol/PEG (5/5/0.03, molar ratio) in which Compound 3 of the present invention is the main component (liposome 3). As described in Example 5, αGluGlu2C16 (1,5-hexadecyl-N-glutamyl-L-glutamate) is a compound having one zwitterionic functional group in the hydrophilic moiety represented by the following formula:

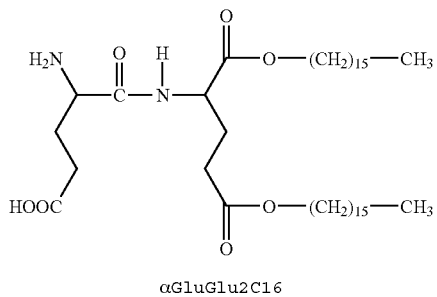

αGluGlu2C16

In this regard, 1,5-hexadecyl N-succinyl-L-glutamate (DHSG) is a lipid having a negative charge, and dipalmitoylphosphatidylcholine (DPPC) is a phospholipid.

Figure 13:
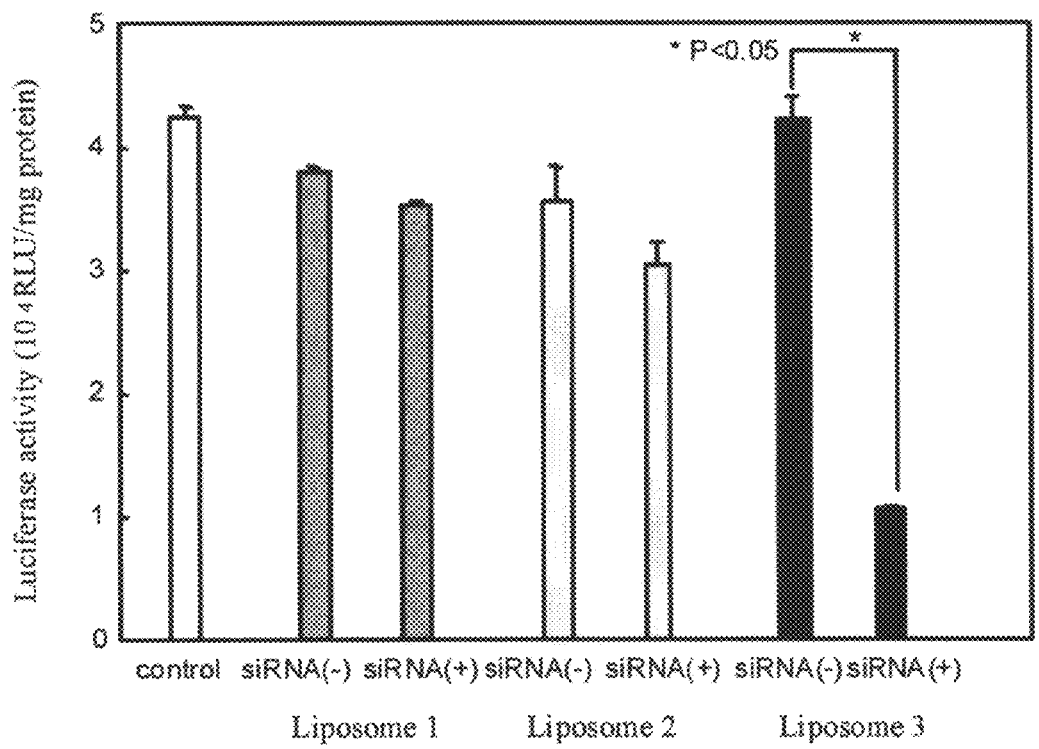
FIG. 13 is a graph showing evaluation results regarding suppression of gene expression in luciferase protein expressing CHO cells caused by siRNA-encapsulated liposome 1 (DPPC/cholesterol/DHSG/PEG-Glu2C18), siRNA-encapsulated liposome 2 (αGluGlu2C16/cholesterol/PEG-Glu2C18) and siRNA-encapsulated liposome 3 (Compound 3/cholesterol/PEG-Glu2C18).

Each of the siRNA-encapsulated liposomes was added to a CHO cell in which the luciferase protein synthesis gene is constantly expressed, and then synthesis inhibition by RNAi was evaluated as described below. Firstly, $5\times10^4$ luciferase expressing CHO cells were seeded in a 12-well plate and cultured for 24 hours (37° C., 5% $CO_2$). After that, the siRNA-encapsulated liposome was added to the cells in the presence of serum ([lipid]=200 µg/well) and cultured for 24 hours (37° C., 5% $CO_2$). After washed with PBS(−) twice, the cells were solubilized. Then the luminescence intensity after substrate addition was measured, and the expression level of luciferase was calculated. The results are shown in FIG. 13. As a control, only medium was added. In FIG. 13, the siRNA-encapsulated liposome is represented by siRNA(+), and the liposome in which siRNA is not encapsulated is represented by siRNA(−).

In the case where there were only luciferase expressing CHO cells, the expression level of luciferase was about $4.2\times10^4$ RLU/µg-protein. In the case of the siRNA-encapsulated liposome 1 (DPPC/cholesterol/DHSG/PEG-Glu2C18), the expression level slightly decreased, but it was almost the same as the expression level at the time of addition of siRNA-nonencapsulated liposome 1. Therefore, it was considered that inhibition by the encapsulated siRNA did not occur in the case of the liposome 1.

On the other hand, in the case of the siRNA-encapsulated liposome 2 (αGluGlu2C16/cholesterol/PEG-Glu2C18) or the liposome 3 (GGLG/cholesterol/PEG-Glu2C18), about 15% or 70% inhibition of luciferase synthesis was respectively confirmed compared to the control group. Such inhibition did not occur in the cases of the siRNA-nonencapsulated liposome group. The results mean that inhibition of luciferase synthesis was caused by the encapsulated siRNA. Further, the siRNA delivery efficiency of the liposome 3 was higher than that of the liposome 2.

The molecular assembly of the present invention is useful as a carrier for a drug, probe, nucleic acid, protein, etc. which efficiently releases such a substance from an endosome to the cytoplasm side. It is thought that the molecular assembly of the present invention is sufficiently useful as a pharmaceutical preparation for therapy of various diseases.

The invention claimed is:

1. An amphiphilic molecule represented by the following formula (Ia):

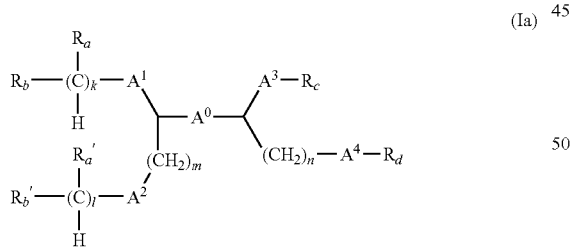

(Ia)

wherein: $R_a$ represents an amino group when the formula has one $R_a$, and when the formula has a plurality of $R_a$s, one $R_a$ represents an amino group and the other $R_a$s represent hydrogen atoms; $R_a'$ represents an amino group when the formula has one $R_a'$, and when the formula has a plurality of $R_a'$s, one $R_a'$ represents an amino group and the other $R_a'$s represent hydrogen atoms; $R_b$ and $R_b'$ each independently represent a carboxyl group; $R_c$ and $R_d$ each independently represent a chain hydrocarbon group having 8 to 22 carbon atoms; $A^0$, $A^1$, and $A^2$ each independently represent —CONH—; $A^3$ and $A^4$ each independently represent —COO—; and k, l, m, and n each independently represent an integer from 1 to 4.

2. The amphiphilic molecule according to claim 1, wherein in an aqueous solution, the amino group and the carboxyl group are independently ionized under a physiological pH environment to become a cation or an anion, and wherein ionization tendency of the carboxyl group is diminished under an acidic pH environment, and wherein ionization tendency of the amino group is diminished under a basic pH environment.

3. The amphiphilic molecule according to claim 1, wherein the amino group is selected from the group consisting of a primary amino group, a secondary amino group, a tertiary amino group and a quaternary ammonium salt.

4. The amphiphilic molecule according to claim 1, wherein the chain hydrocarbon group is selected from the group consisting of a myristyl group, a palmityl group, a stearyl group and an oleyl group.

5. An amphiphilic molecule represented by any one of the following formulae (Ia-1) to (Ia-8):

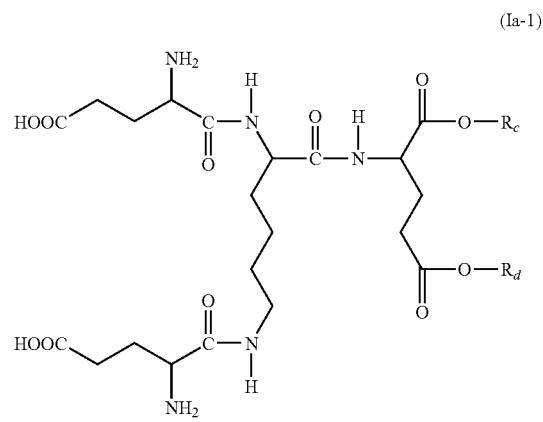

(Ia-1)

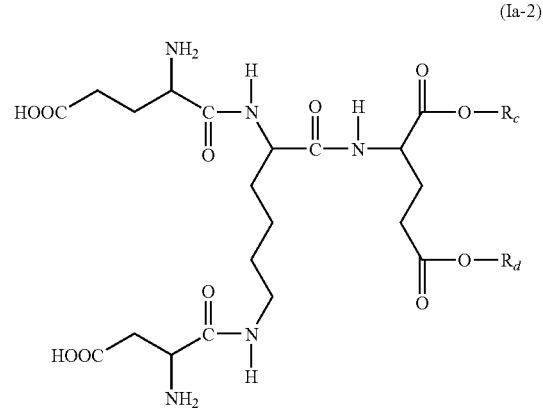

(Ia-2)

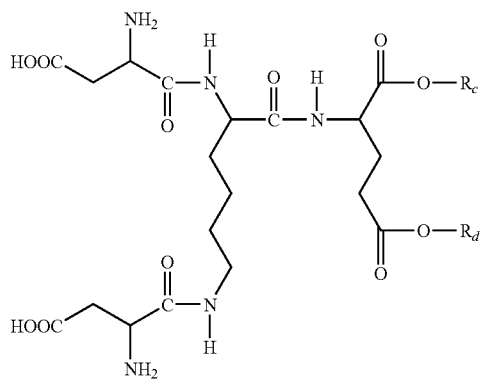
(Ia-3)

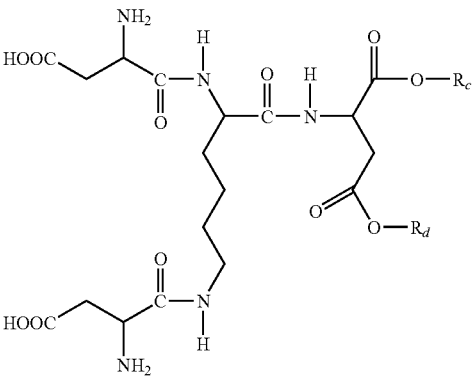
(Ia-7)

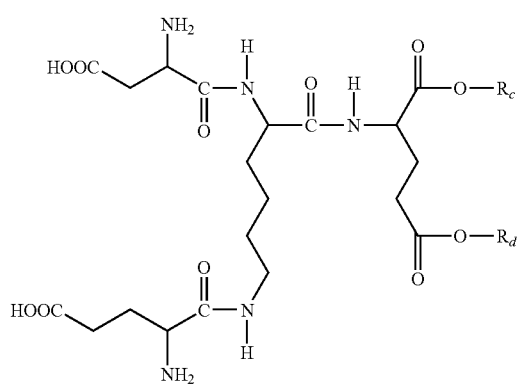
(Ia-4)

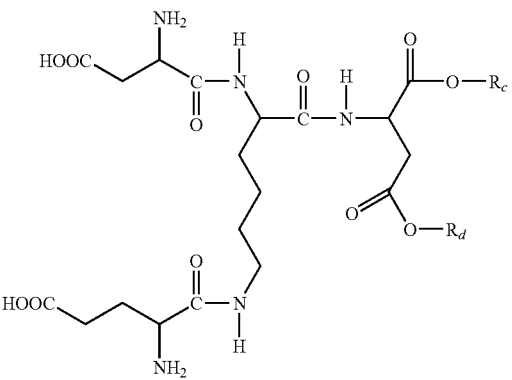
(Ia-8)

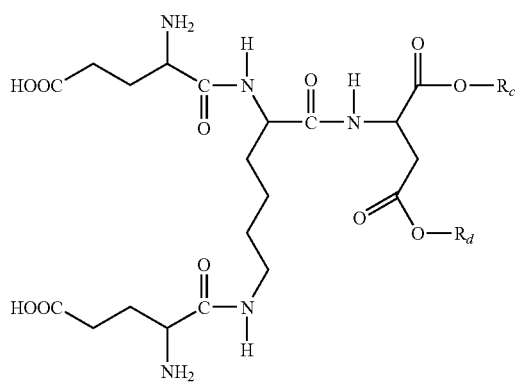
(Ia-5)

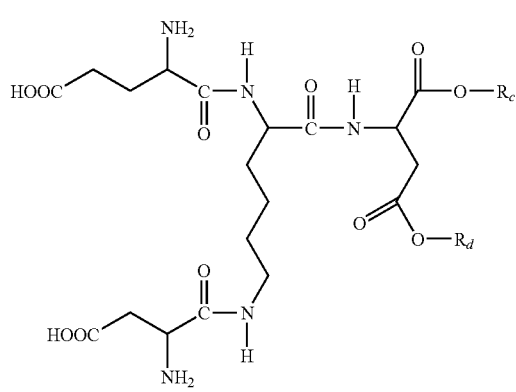
(Ia-6)

wherein $R_c$ and $R_d$ each independently represent a chain hydrocarbon group having 8 to 22 carbon atoms.

6. The amphiphilic molecule according to claim 5, wherein in an aqueous solution, —NH₂ becomes —NH₃⁺ and —COOH becomes —COO⁻ under a physiological pH environment to exhibit zwitterionic properties, and wherein ionization tendency of —COOH is diminished under an acidic pH environment, and wherein ionization tendency of —NH₂ is diminished under a basic pH environment.

7. A molecular assembly comprising the amphiphilic molecule according to claim 1.

8. The molecular assembly according to claim 7, which forms a vesicular structure for carrying a substance of interest, wherein the zeta potential becomes neutral or negative under a physiological pH environment, wherein the zeta potential becomes positive under an acidic pH environment, and through interaction with an anionic biomembrane, the vesicular structure is deformed to release the substance of interest to the outside of the vesicular structure.

9. The molecular assembly according to claim 8, which releases the substance of interest to the outside of an endosome when taken into a cell by endocytosis.

10. The molecular assembly according to claim 7, which carries at least one substance selected from the group consisting of a drug, a probe, a nucleic acid, a protein, a peptide, a metal ion and a metal complex.

11. A reagent comprising the molecular assembly according to claim 7, which carries a probe or nucleic acid.

12. The reagent according to claim 11, which controls gene expression in a cell.

13. A kit comprising the reagent according to claim 11.

14. A protein preparation for enzyme replacement therapy comprising the molecular assembly according to claim 7, which carries a protein.

* * * * *